United States Patent [19]
Hinchliffe et al.

[11] Patent Number: 5,833,698
[45] Date of Patent: *Nov. 10, 1998

[54] ANASTOMOSIS INSTRUMENT AND METHOD

[75] Inventors: Peter W. J. Hinchliffe, New Haven; Keith Ratcliff, Newtown; Kenneth E. Toso, Wilton, all of Conn.

[73] Assignee: United States Surgical Corporation, Norwalk, Conn.

[*] Notice: The term of this patent shall not extend beyond the expiration date of Pat. No. 5,707,380.

[21] Appl. No.: 685,386

[22] Filed: Jul. 23, 1996

[51] Int. Cl.⁶ .................................................. A61B 17/04
[52] U.S. Cl. ......................... 606/153; 606/142; 606/151
[58] Field of Search .................................. 606/142, 143, 606/151, 153, 154; 227/19

[56] References Cited

U.S. PATENT DOCUMENTS

| | | |
|---|---|---|
| 3,366,301 | 1/1968 | Mallina ........................................ 227/19 |
| 3,519,187 | 7/1970 | Kapitanov et al. ...................... 606/153 |
| 3,575,038 | 4/1971 | Mallett . |
| 3,908,662 | 9/1975 | Razgulov et al. . |
| 4,350,160 | 9/1982 | Kolesov et al. . |
| 4,466,436 | 8/1984 | Lee . |
| 4,809,695 | 3/1989 | Gwathmey et al. ...................... 227/19 |
| 4,930,674 | 6/1990 | Barak . |
| 4,979,954 | 12/1990 | Gwathmey et al. ...................... 606/219 |
| 5,234,447 | 8/1993 | Kaster et al. . |
| 5,346,115 | 9/1994 | Perouse et al. . |
| 5,366,462 | 11/1994 | Kaster et al. . |
| 5,403,333 | 4/1995 | Kaster et al. . |
| 5,486,187 | 1/1996 | Schenck ................................... 606/153 |
| 5,501,698 | 3/1996 | Roth et al. ............................... 606/205 |

FOREIGN PATENT DOCUMENTS

WO 95/17127  6/1995  WIPO .
9535065  12/1995  WIPO .

OTHER PUBLICATIONS

European Search Report dated Dec. 30, 1997.

*Primary Examiner*—Gary Jackson

[57] ABSTRACT

A surgical instrument for anastomosis of first and second blood vessels is provided having a handle and a body portion extending distally from the handle. A collet is mounted adjacent a distal end portion of the body portion and defines a passage therethrough for the reception of an end of a first blood vessel. A plurality of surgical fasteners are releasably supported by the collet and radially oriented about the distal end thereof. An anvil is mounted adjacent of the collet. The anvil and collet are relatively slidable in response to actuation of the handle to simultaneously deform then release the surgical fasteners.

38 Claims, 24 Drawing Sheets

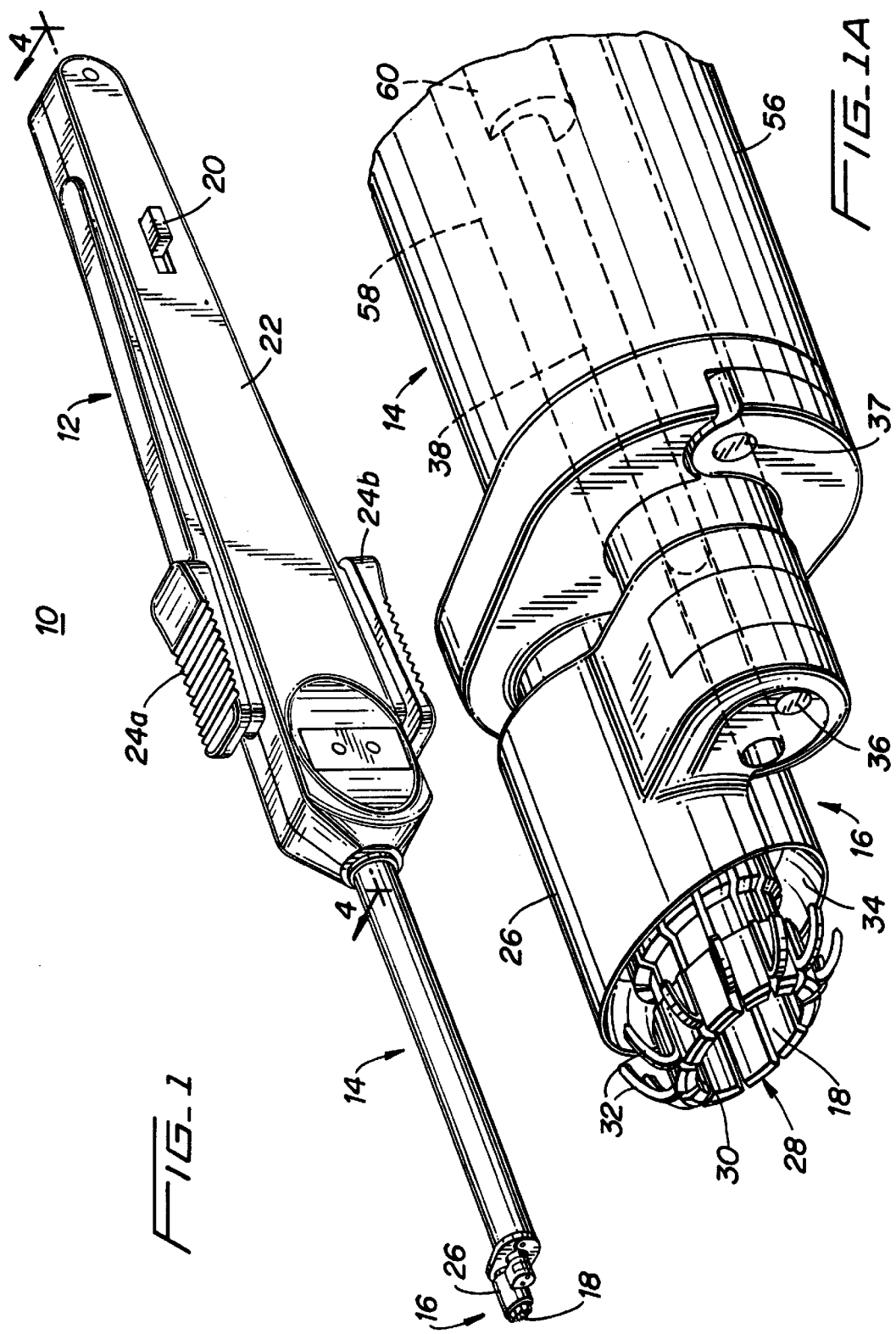

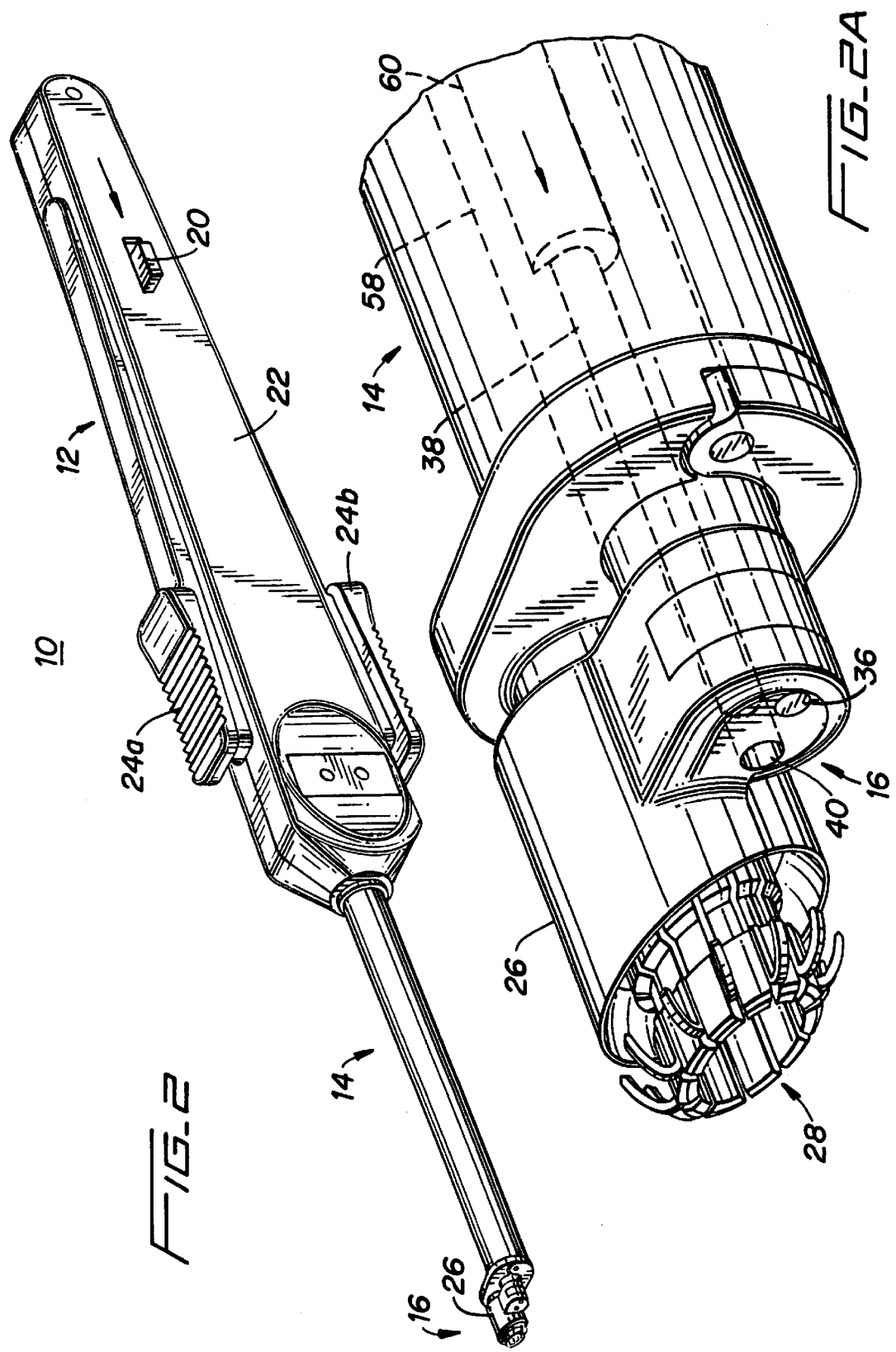

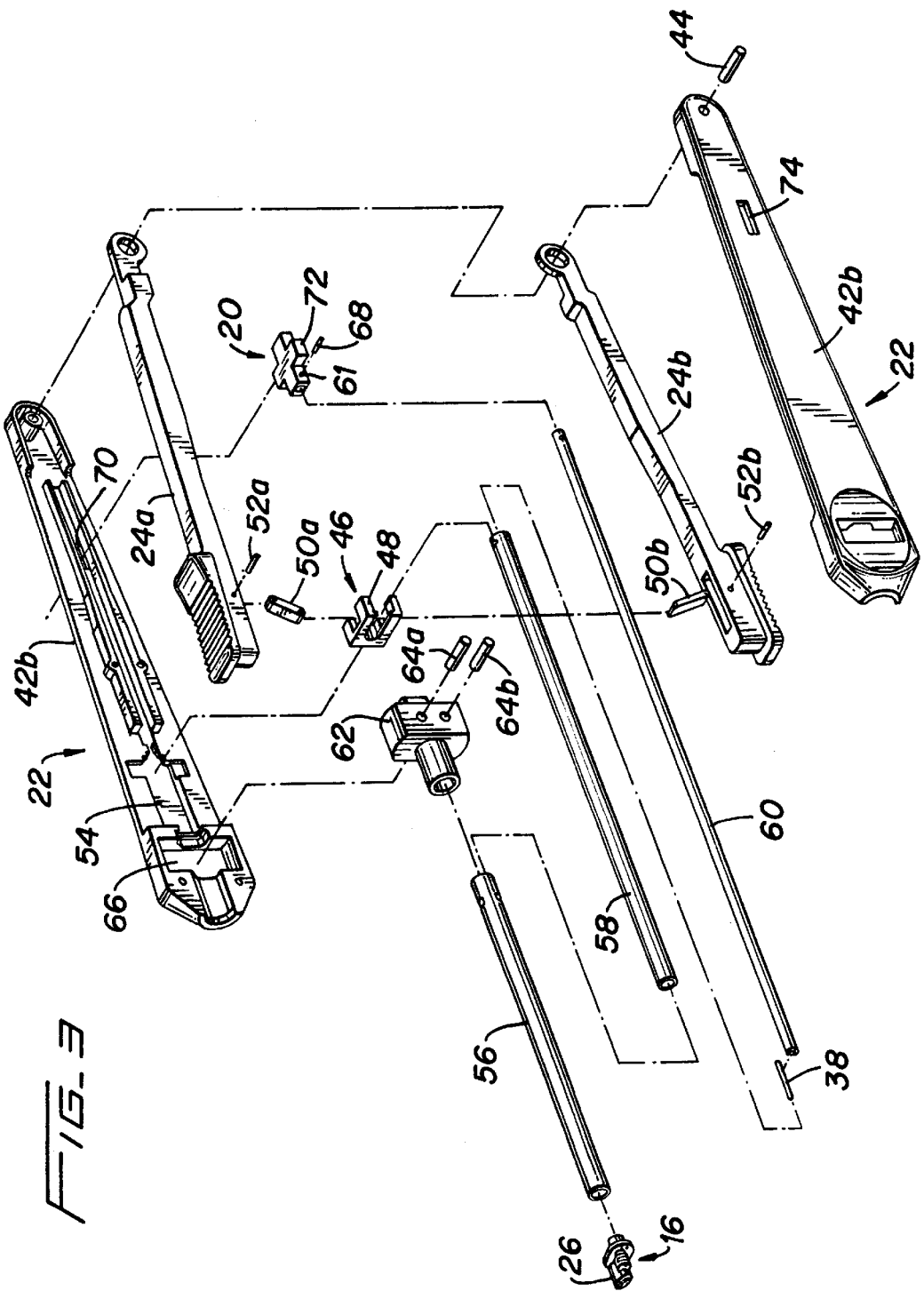

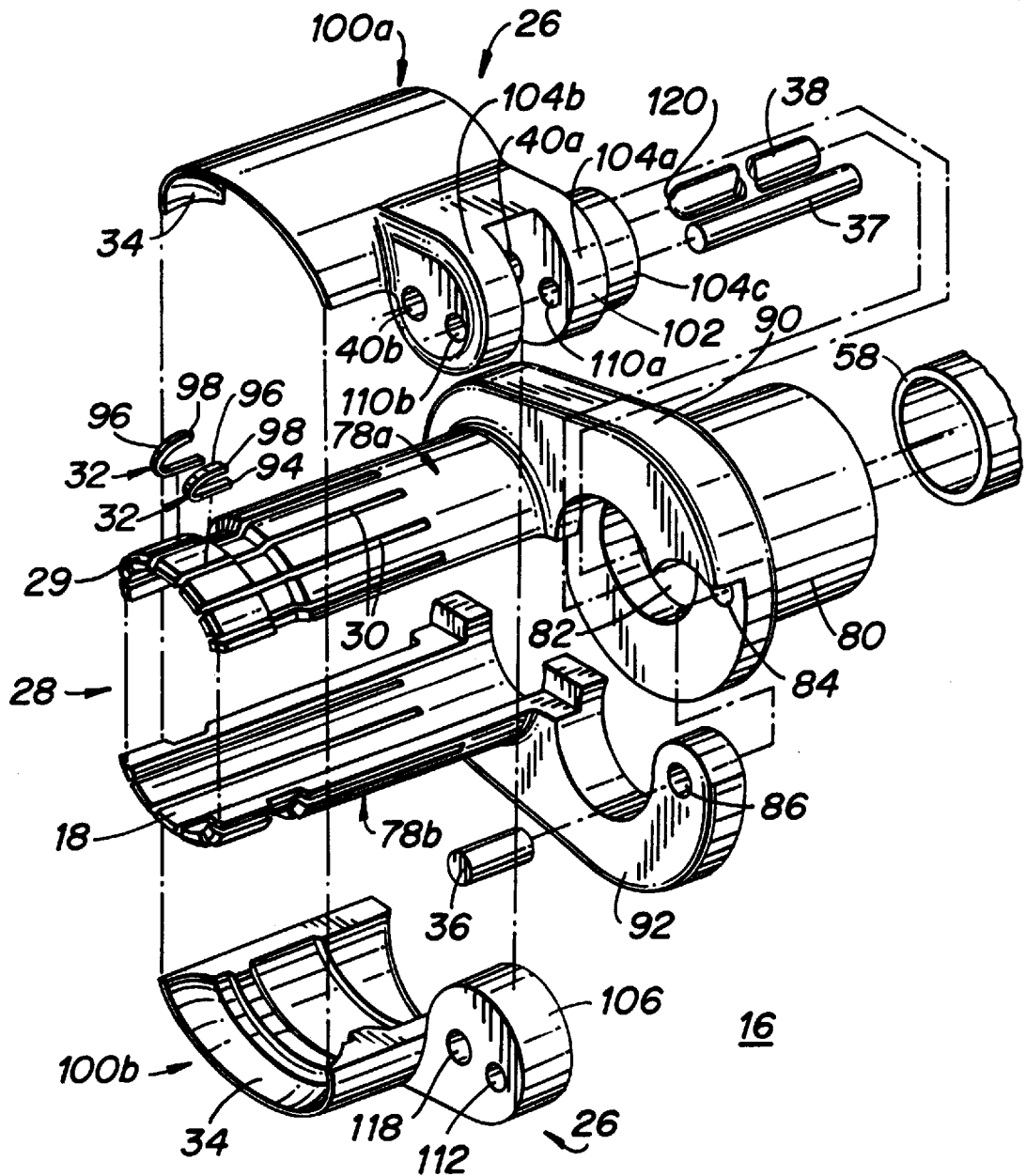

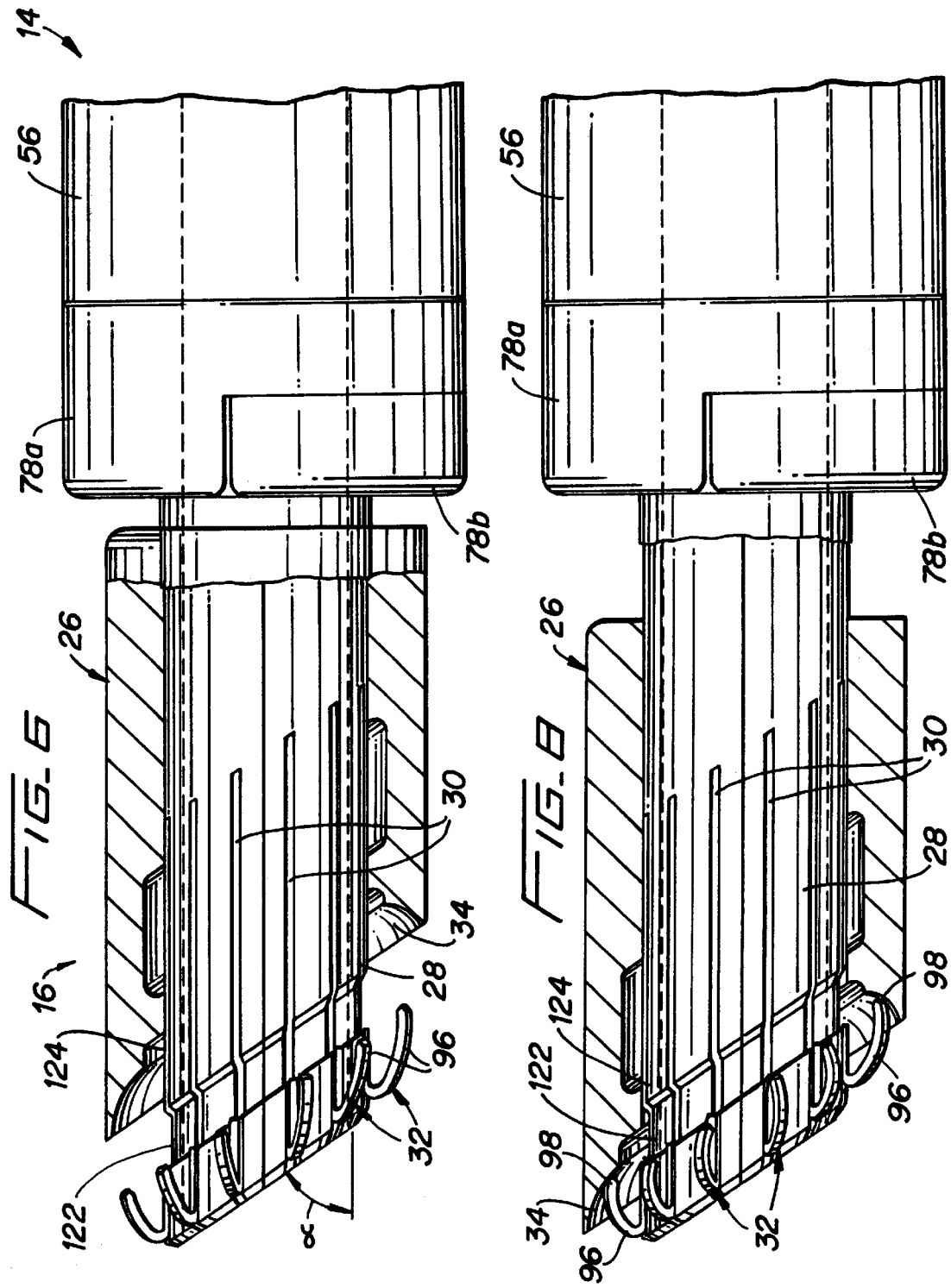

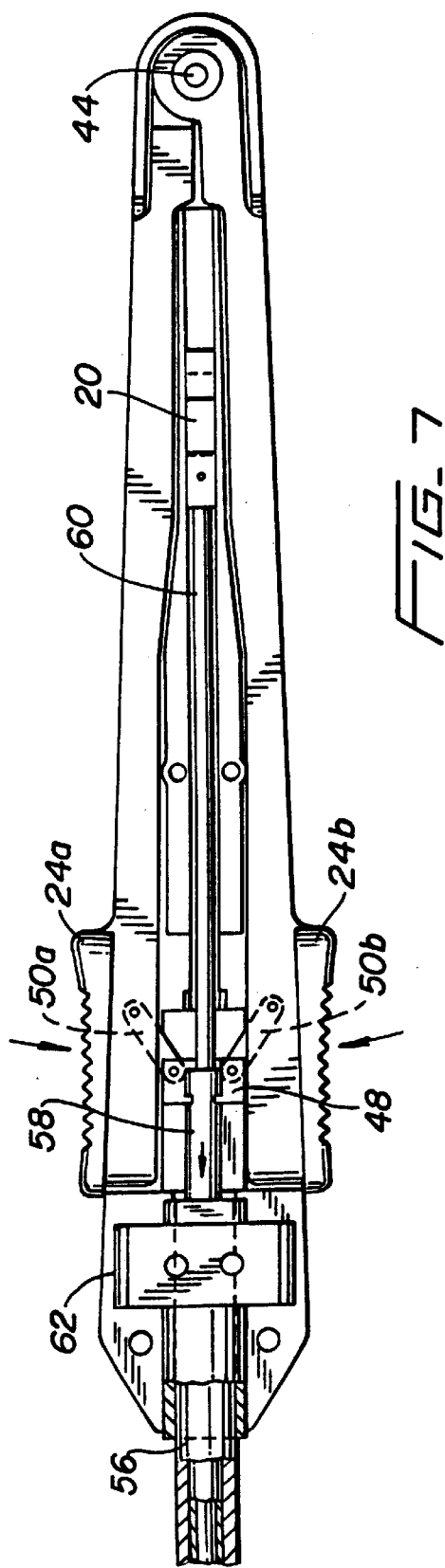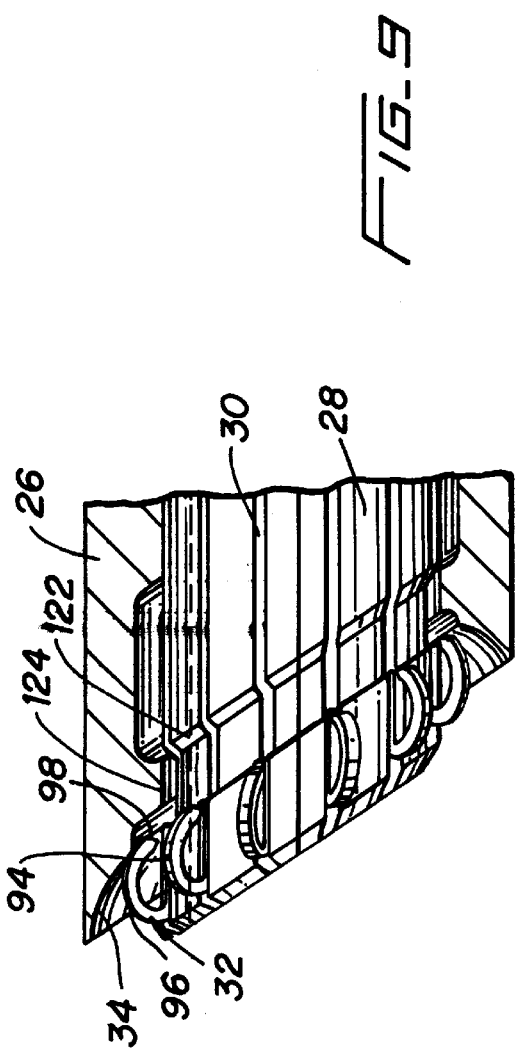

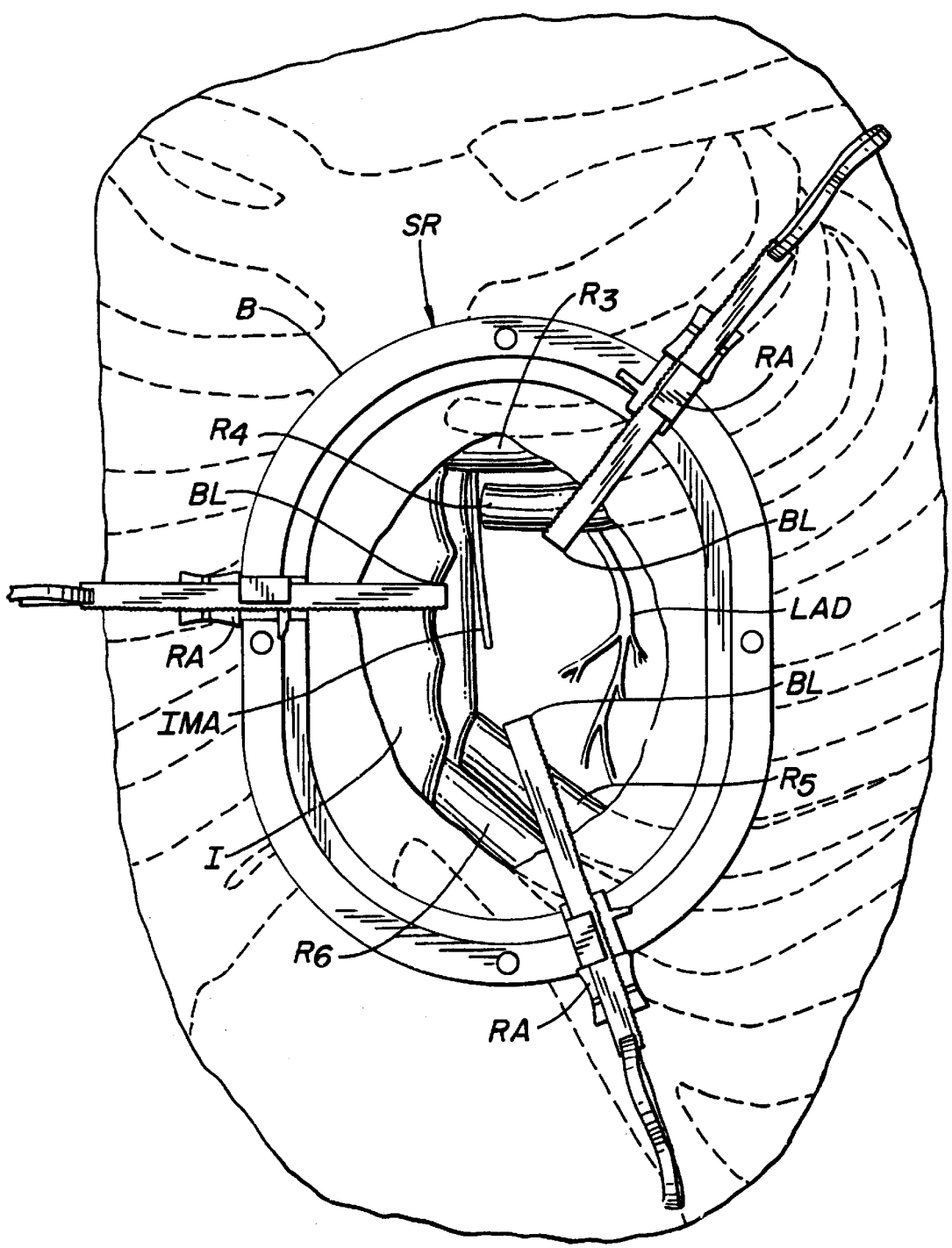
FIG_10

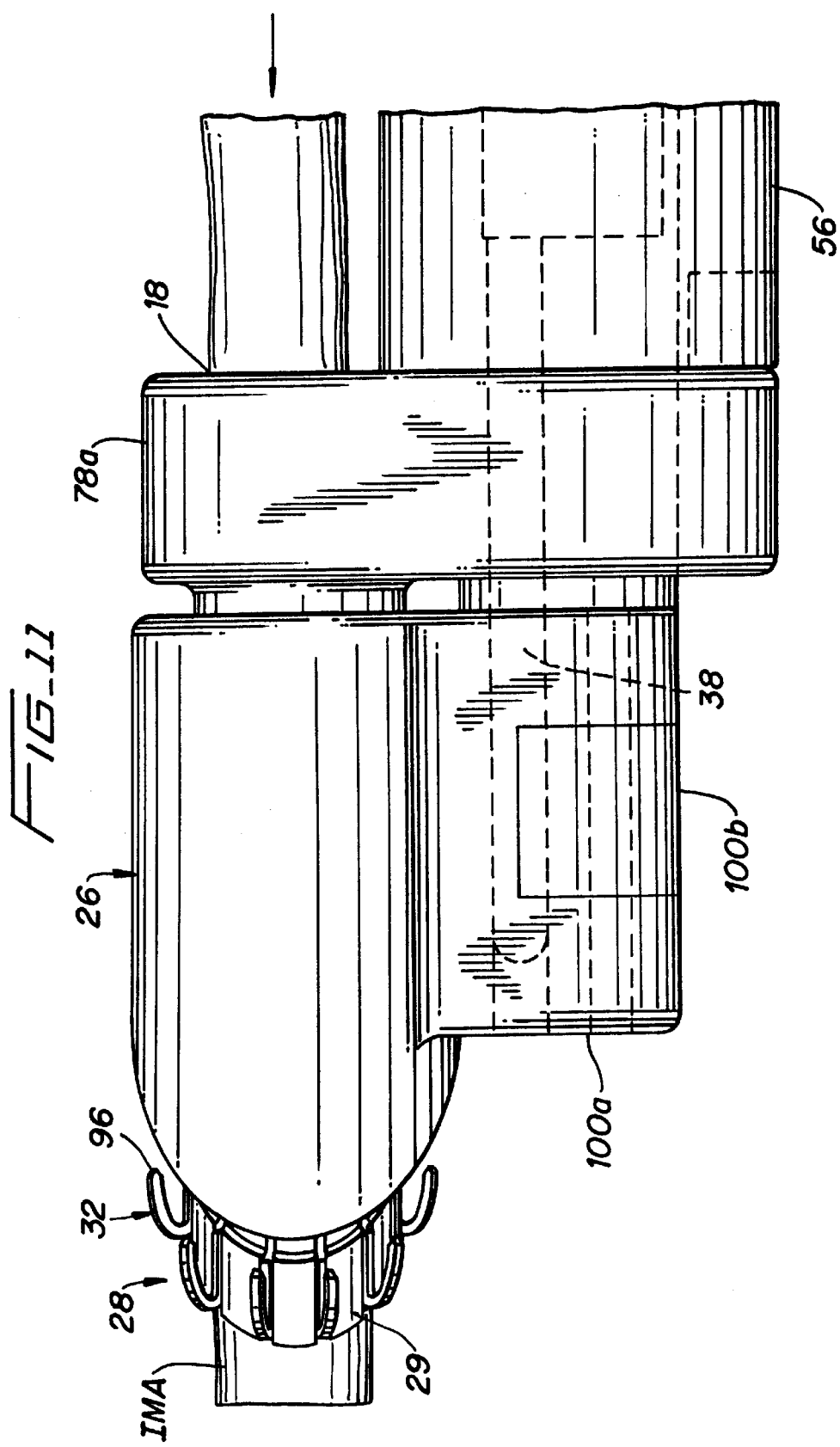

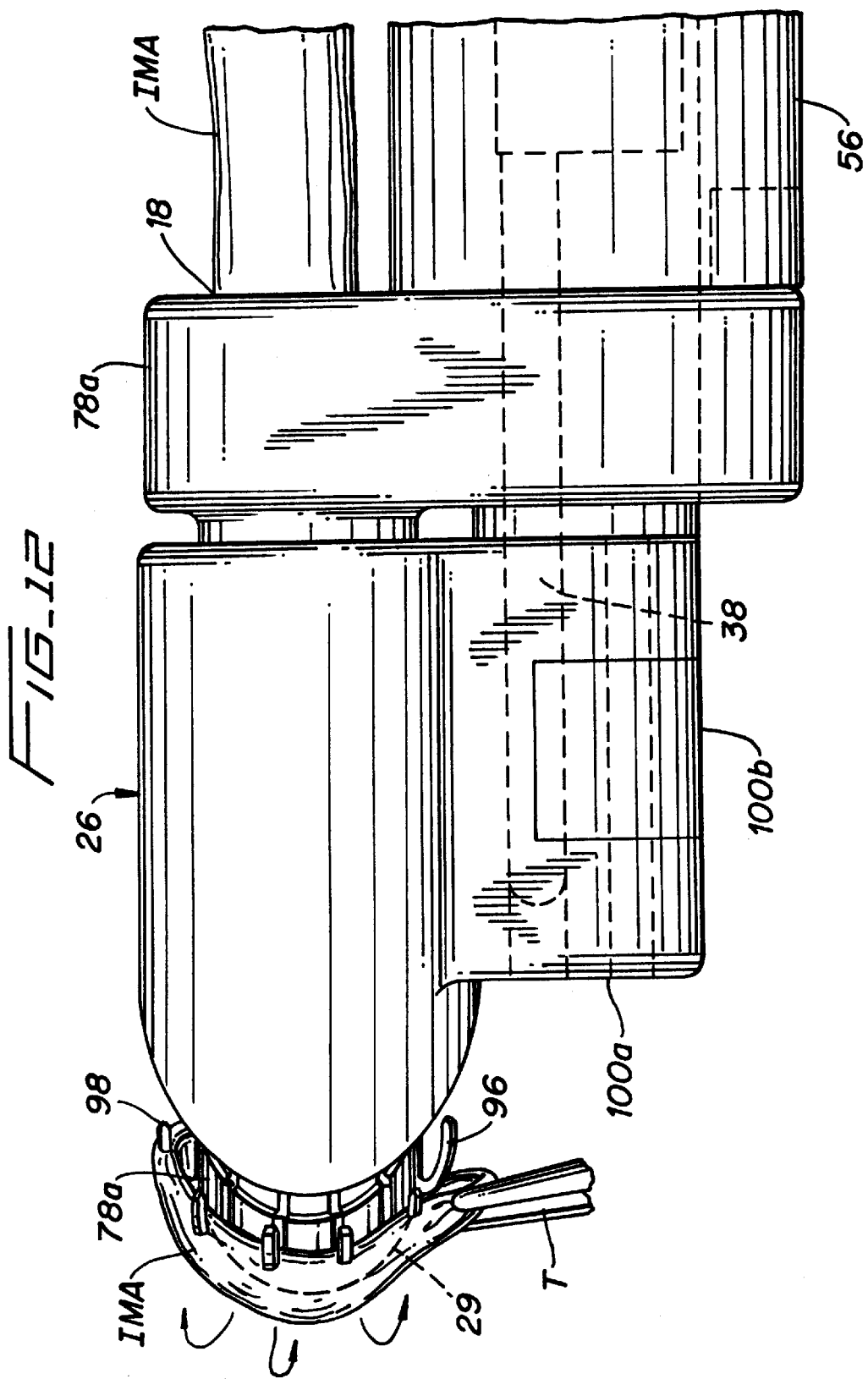

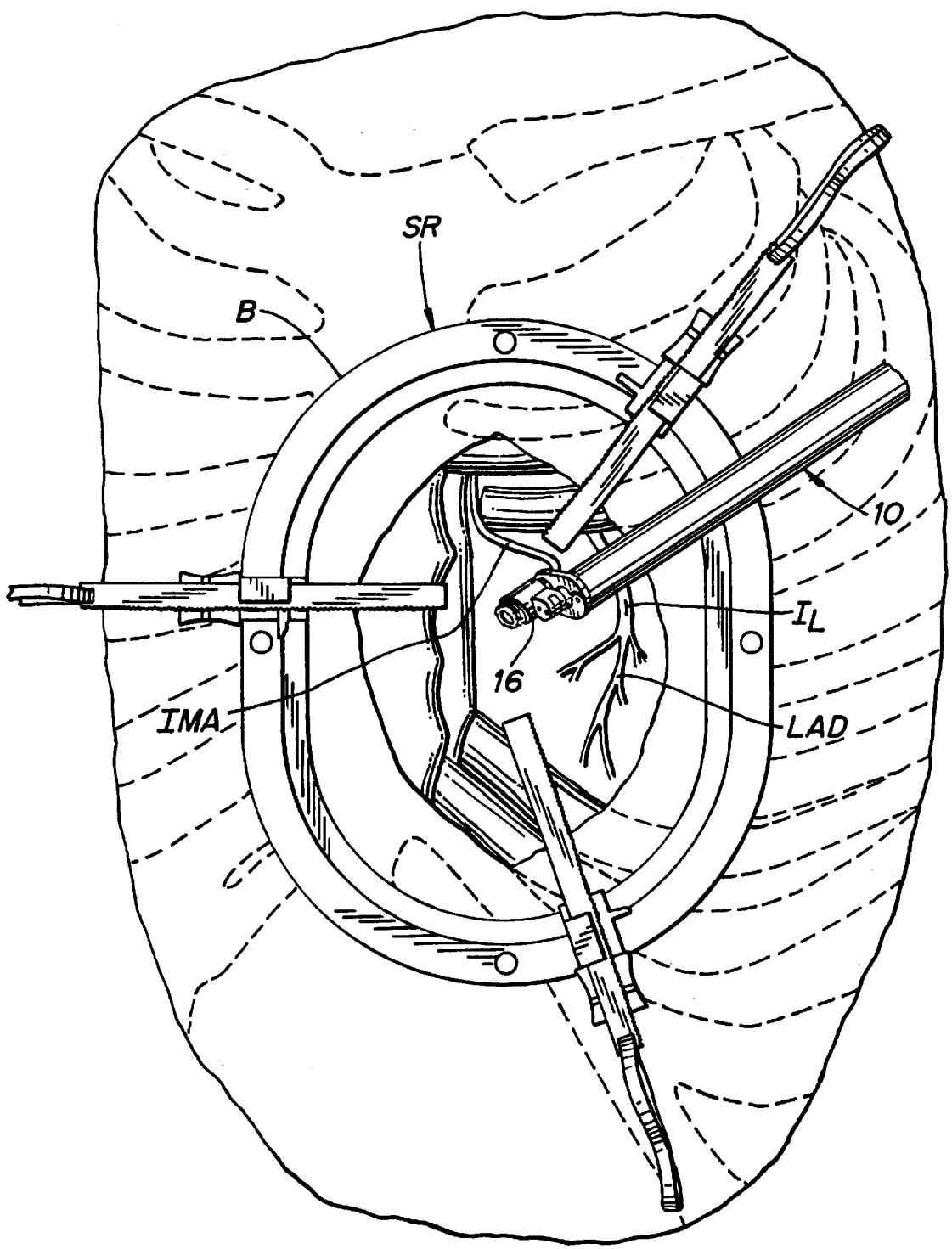

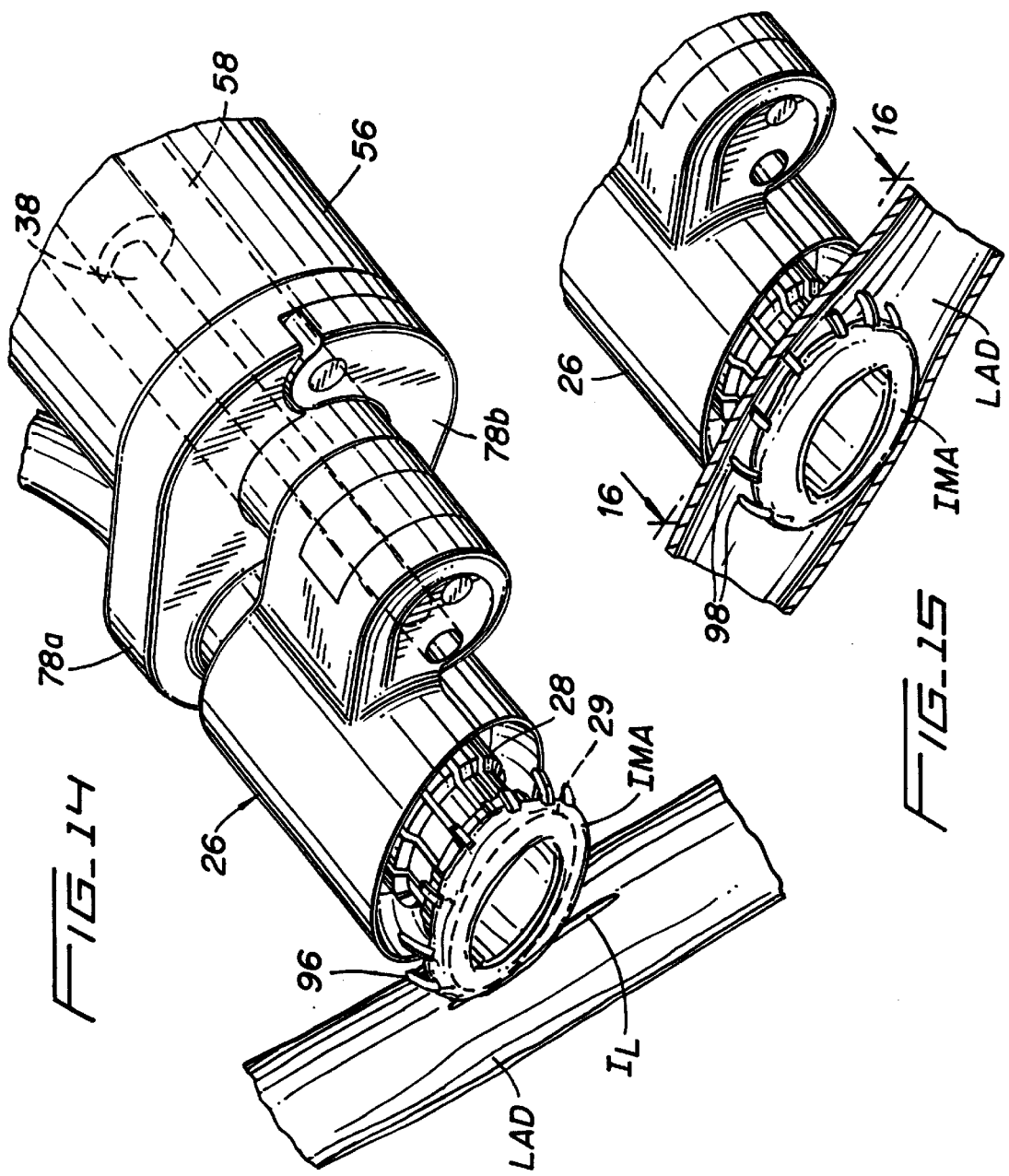

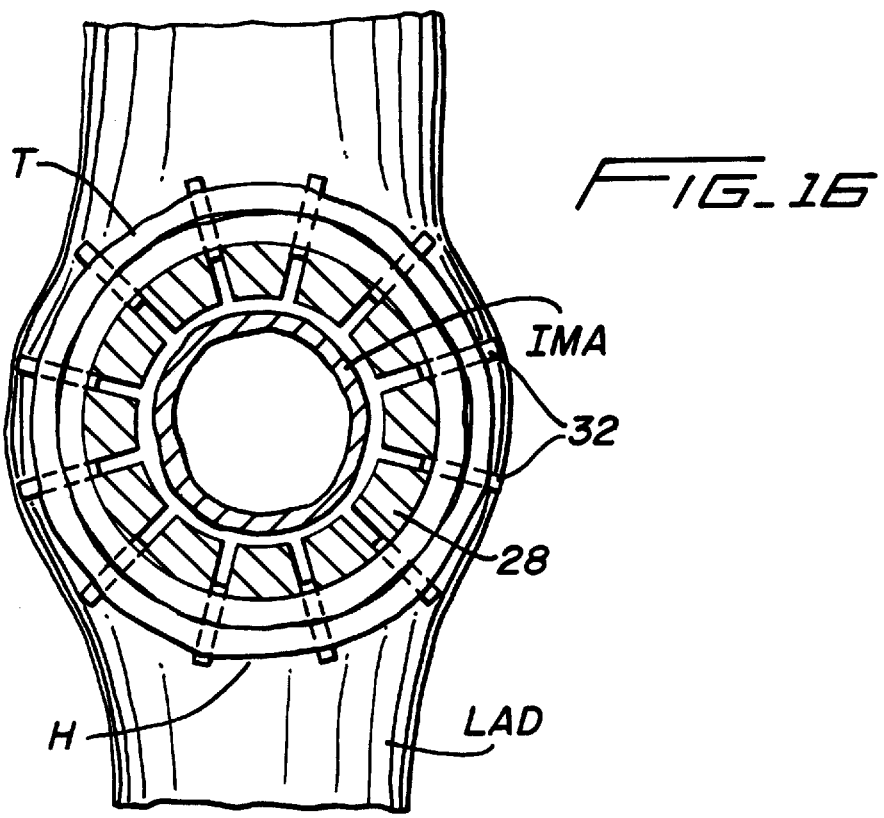
FIG_16
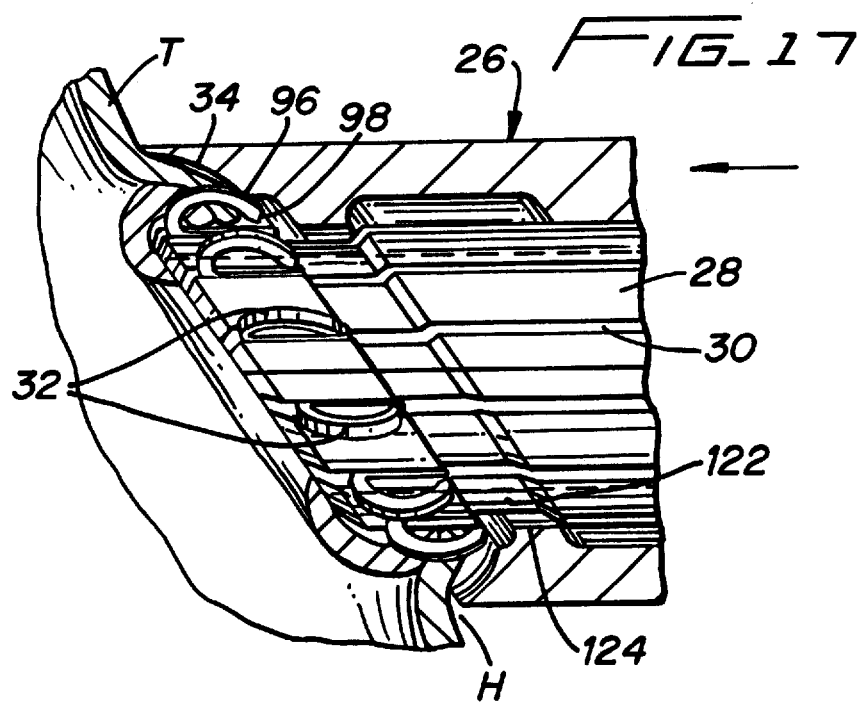
FIG_17

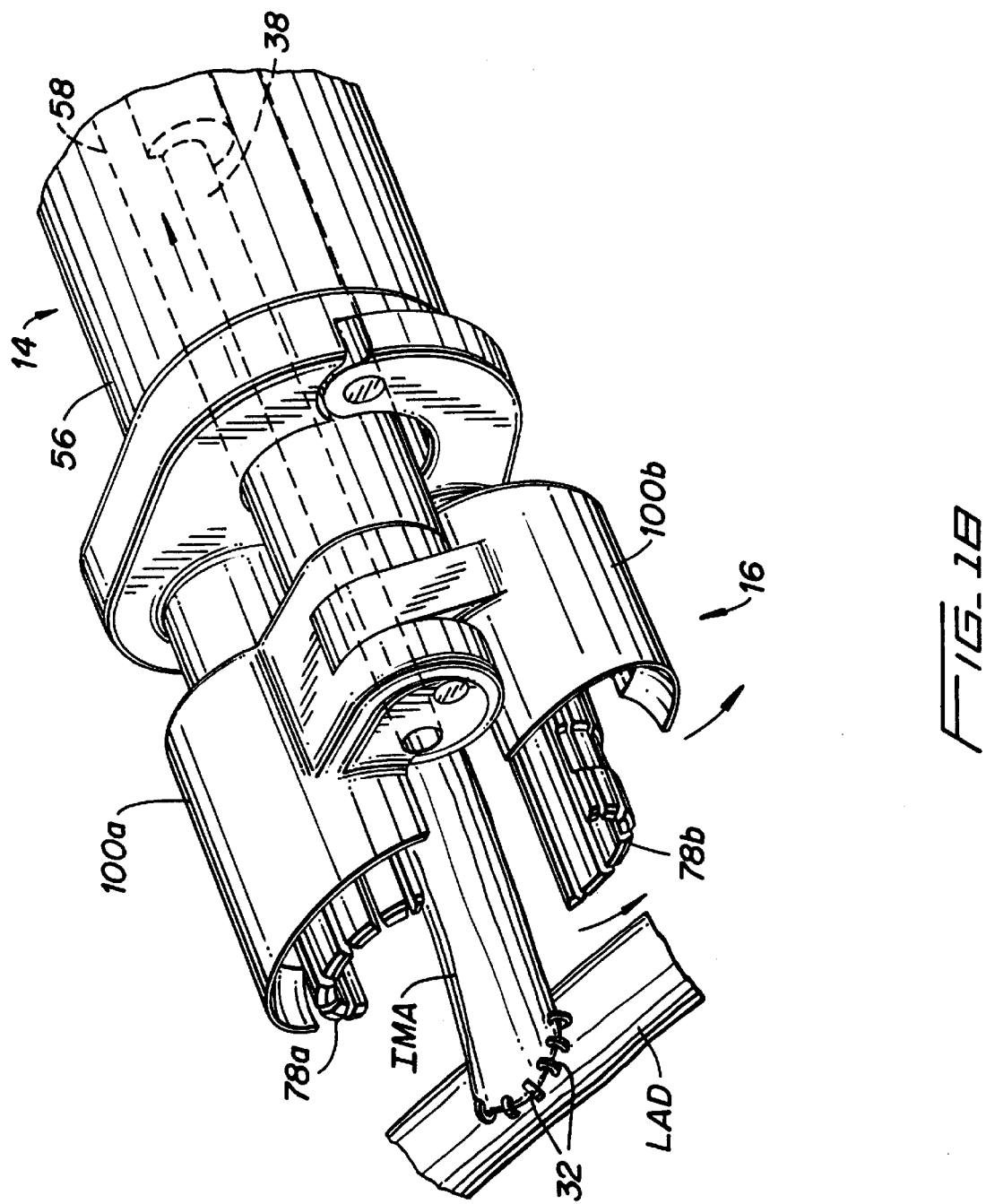

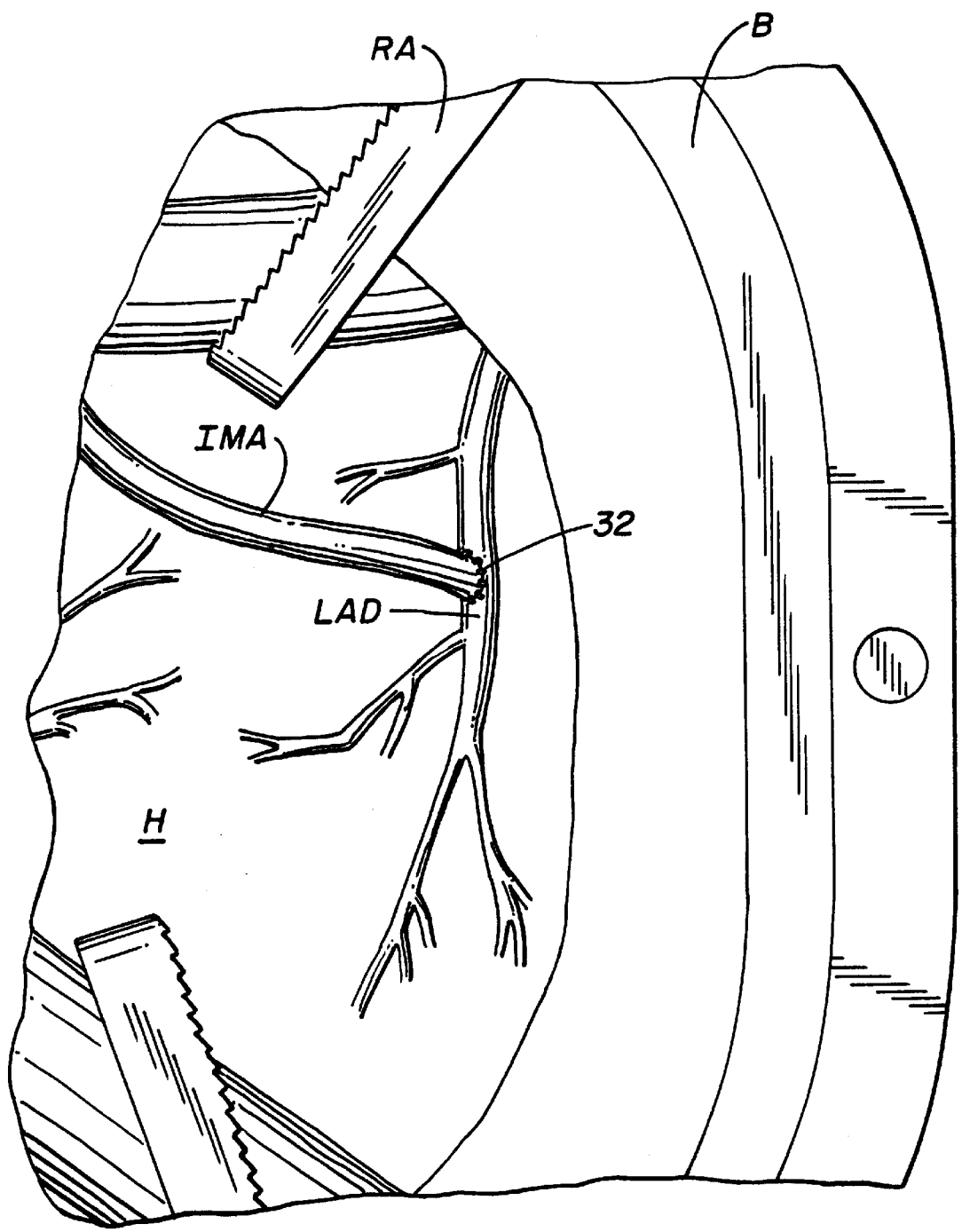
FIG_19

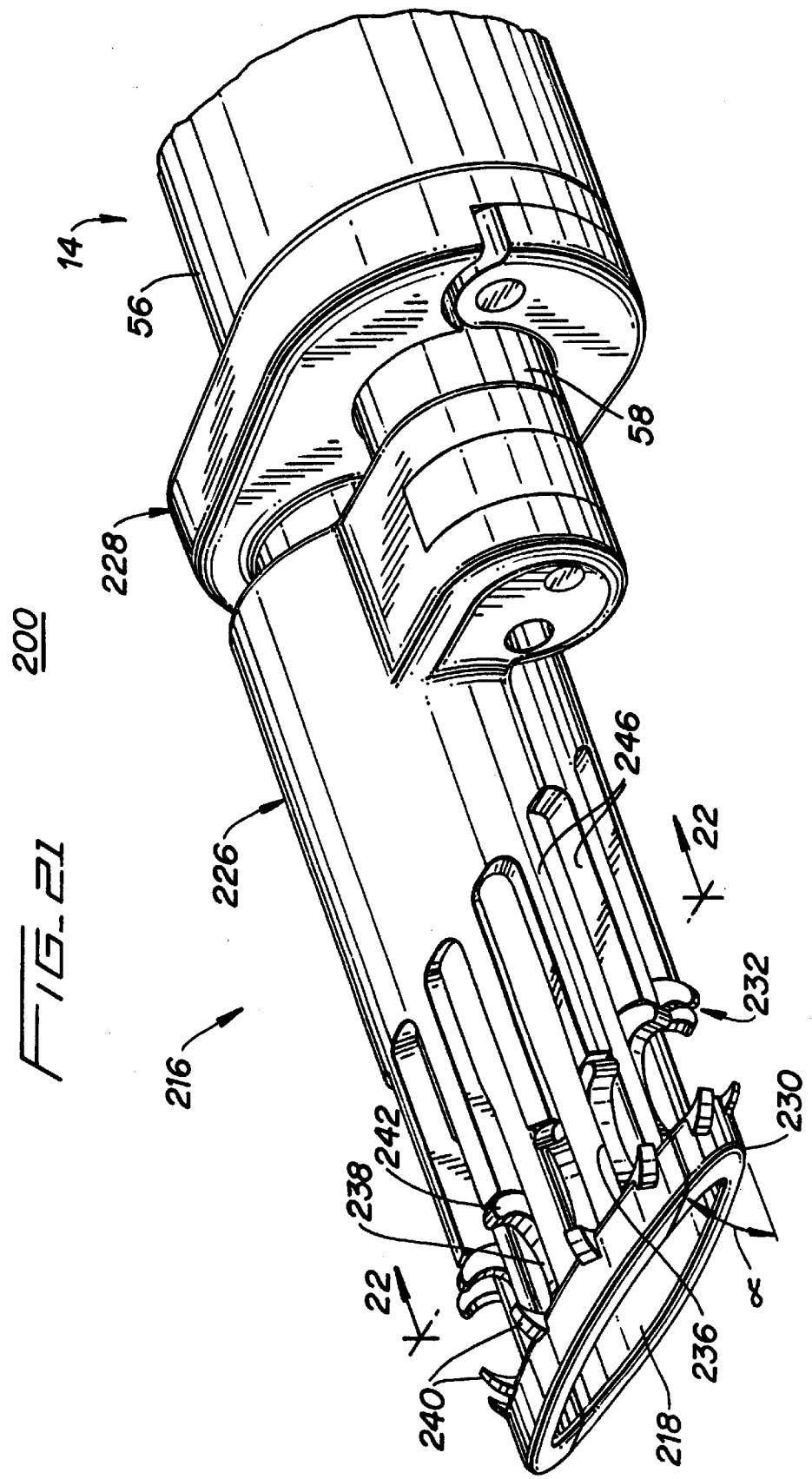

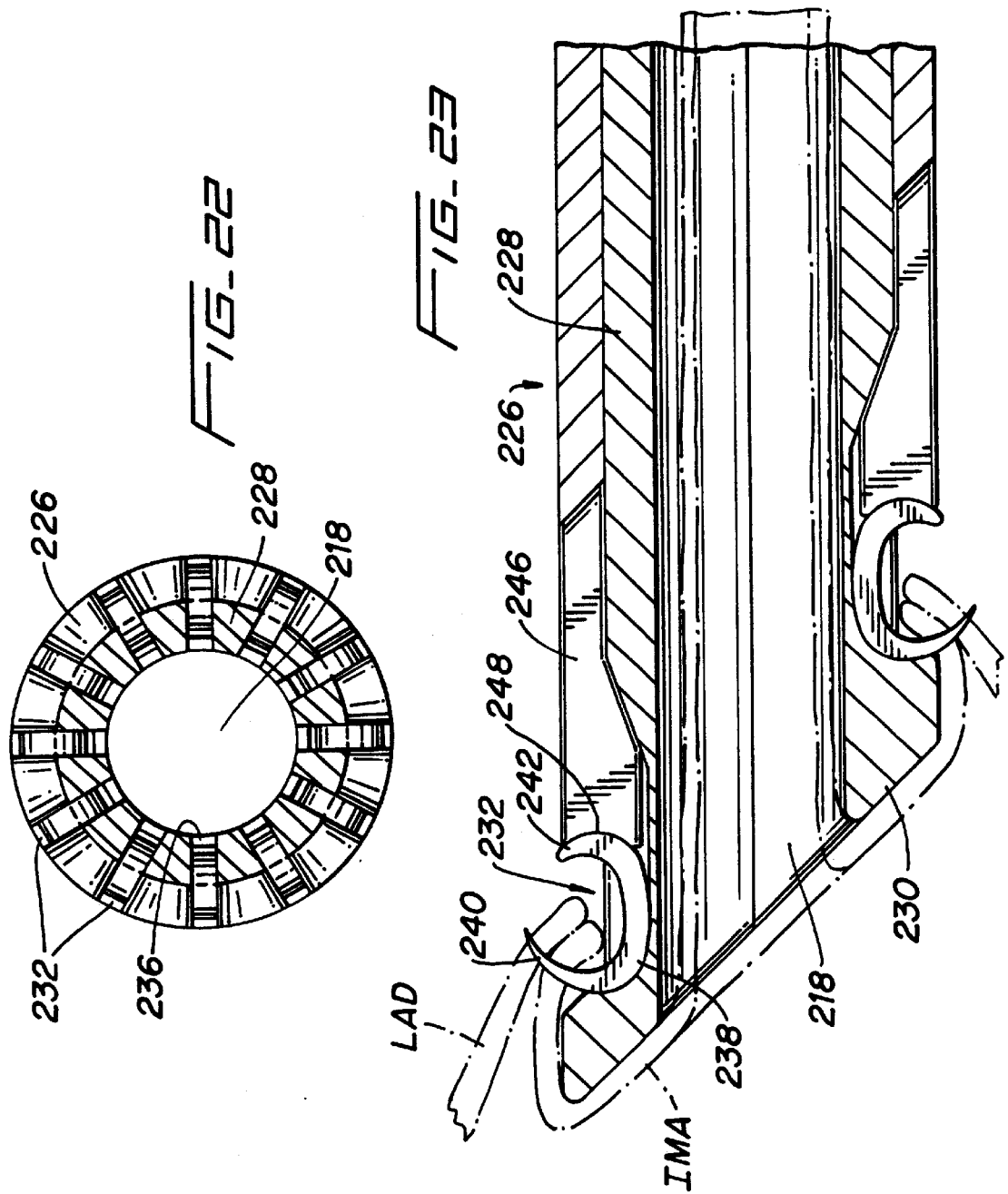

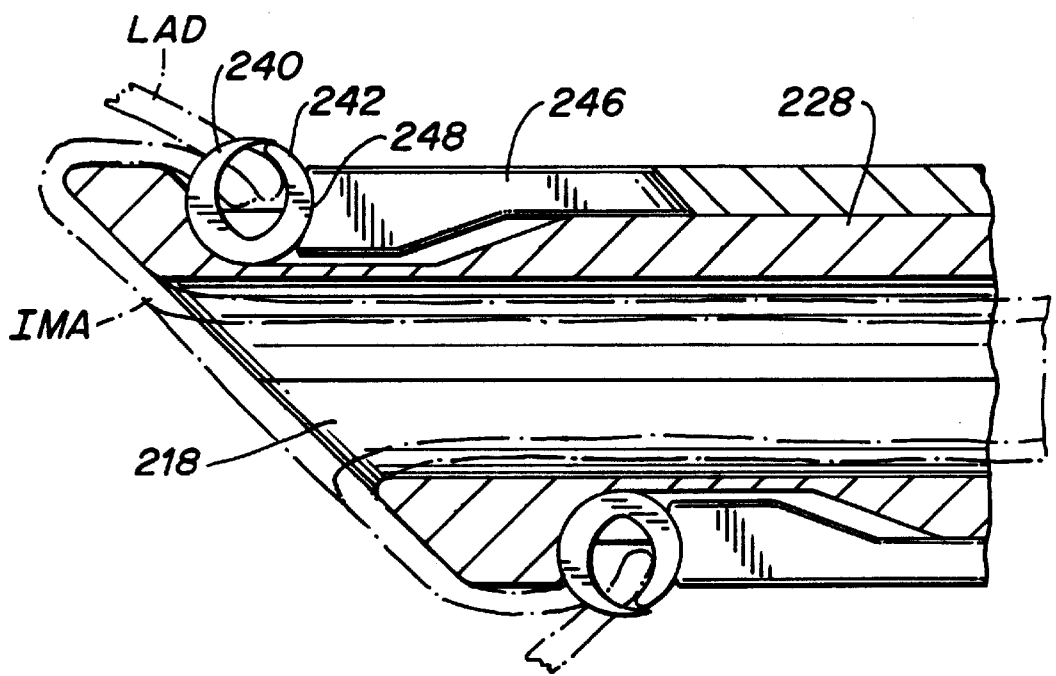

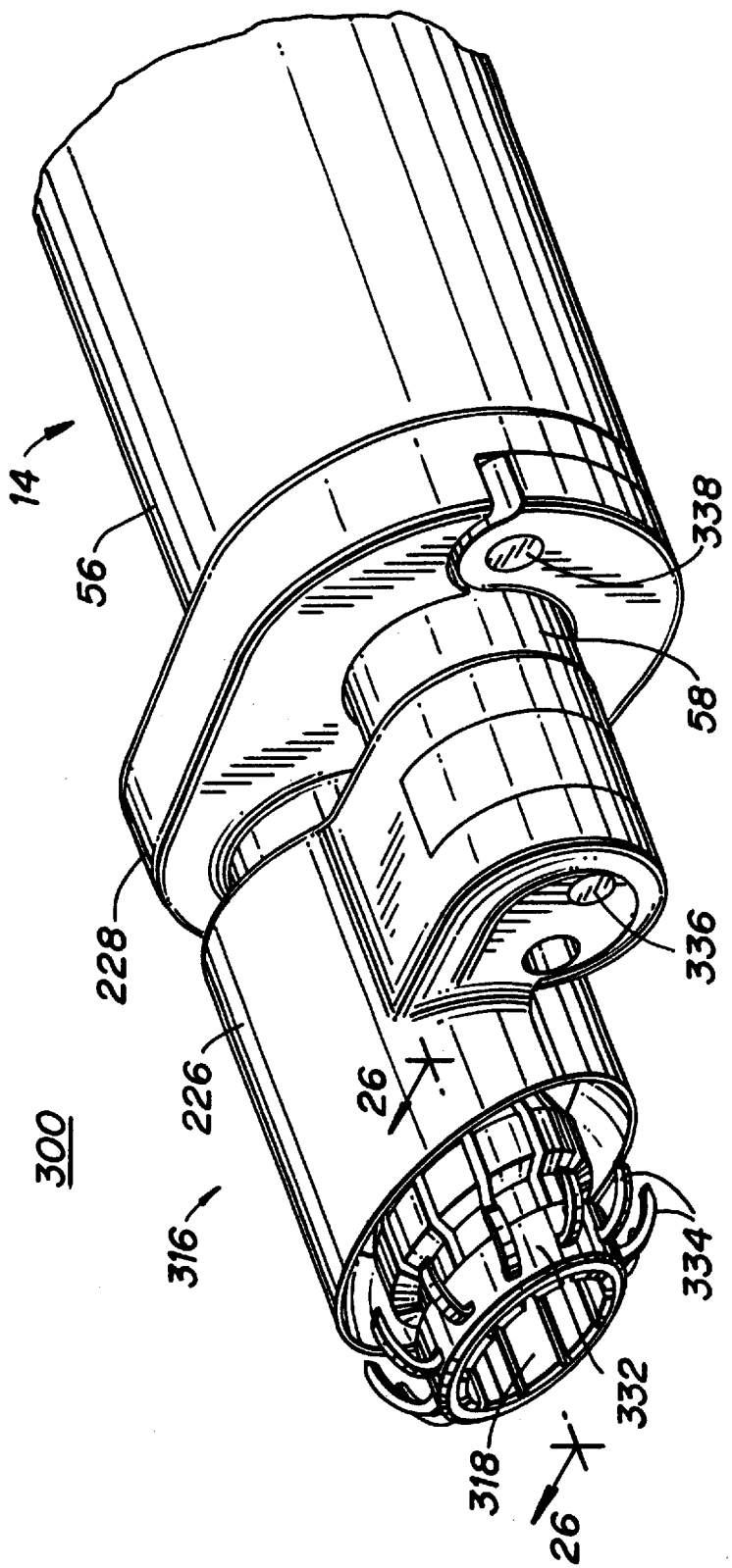

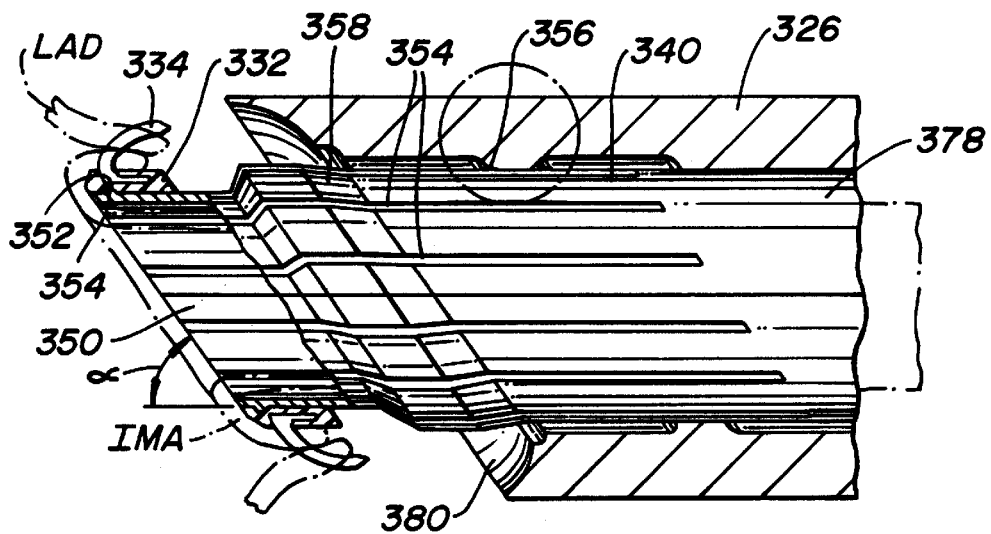
FIG_26
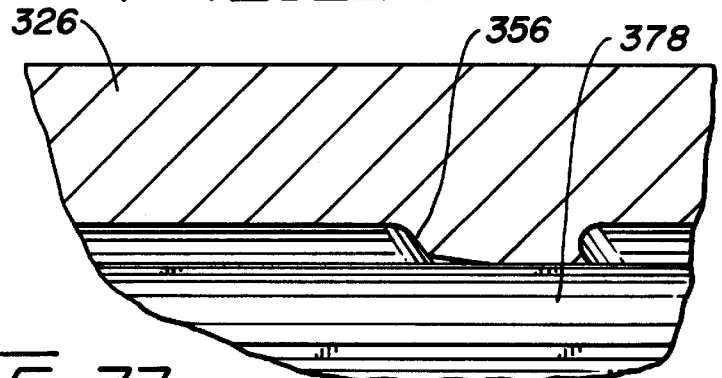
FIG_26A
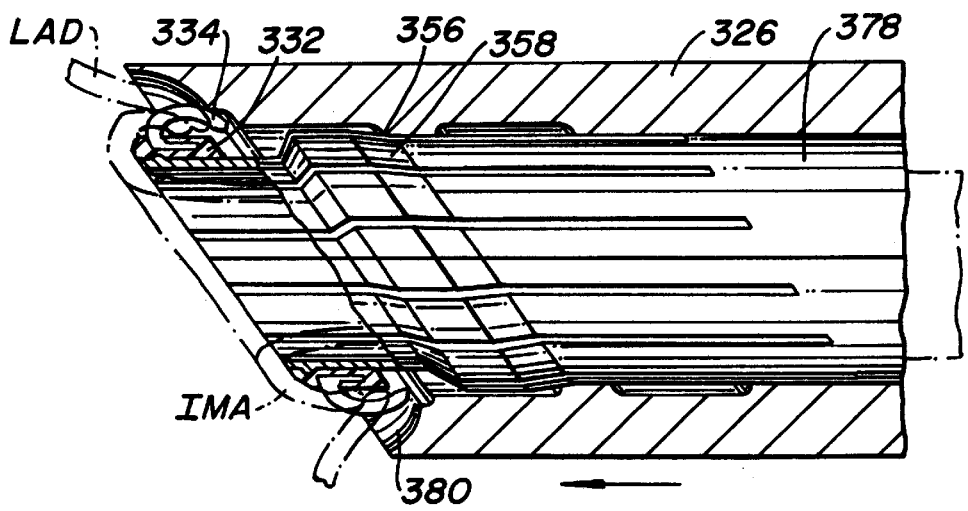
FIG_27

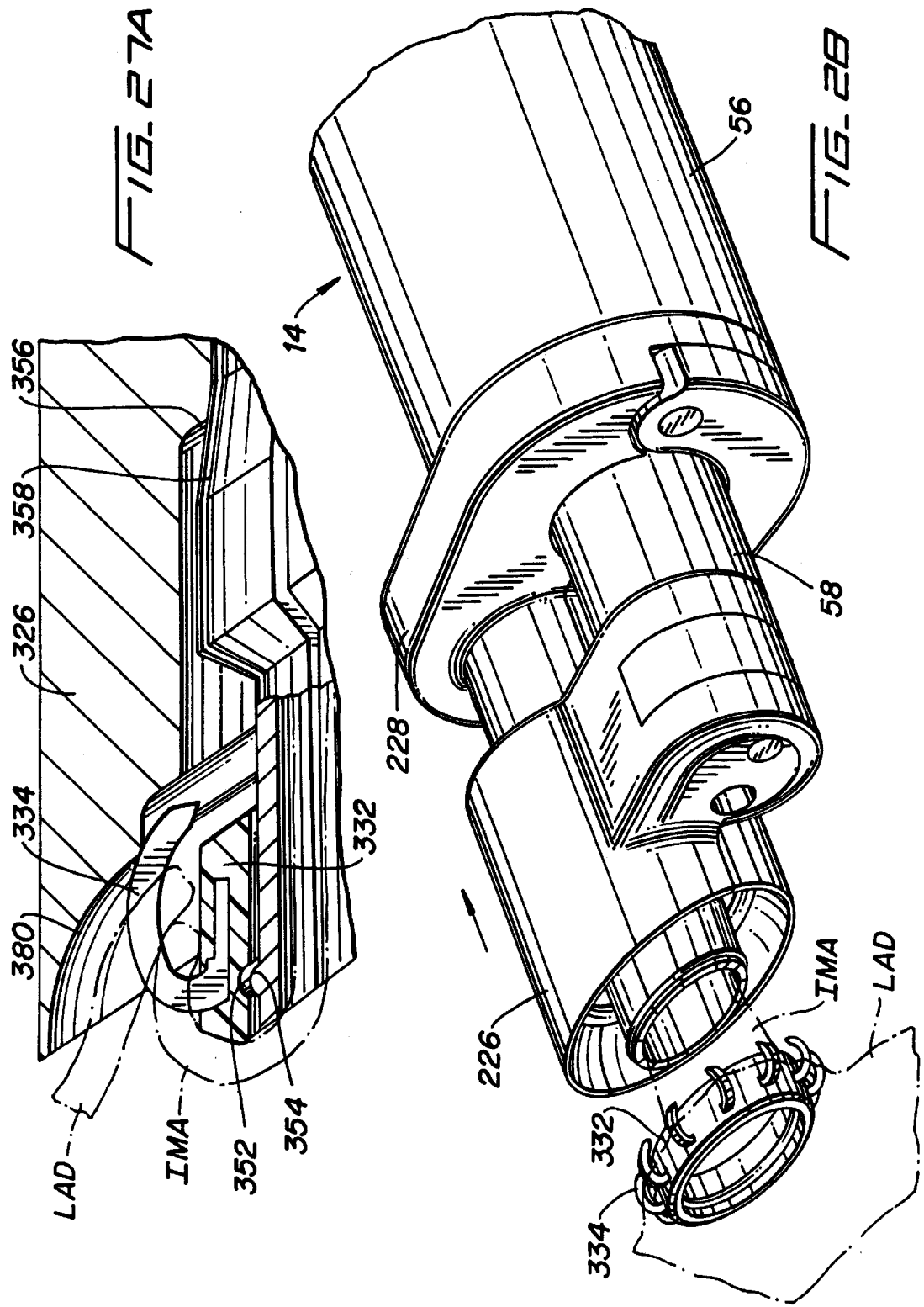

ANASTOMOSIS INSTRUMENT AND METHOD

BACKGROUND

1. Technical Field

The subject disclosure relates to a surgical apparatus and method for performing anastomosis of tubular body structures, and more particularly to an instrument for joining vascular tissues.

2. Background of Related Art

Coronary artery disease is often characterized by lesions or occlusions in the coronary arteries which may result in inadequate blood flow to the myocardium, or myocardial ischemia, which is typically responsible for such complications as angina pectoris, necrosis of cardiac tissue (myocardial infarction), and sudden death. In some cases, coronary artery disease may be treated by the use of drugs and by modifications in behavior and diet. In other cases, dilatation of coronary arteries may be achieved by such procedures as angioplasty, laser ablation, atherectomy, catheterization, and intravascular stents.

For certain patients, coronary artery bypass grafting (CABG) is the preferred form of treatment to relieve symptoms and often increase life expectancy. CABG consists of direct anastomosis of a vessel segment to one or more of the coronary arteries. For example, a reversed segment of the saphenous vein may be grafted at one end to the ascending aorta as an arterial blood source and at the other end to a coronary artery at a point beyond the arterial occlusion. Alternatively, the internal mammary artery (IMA) is located in the thoracic cavity adjacent the sternum and is likewise suitable for grafting to a coronary artery, such as the left anterior descending artery (LAD).

The performance of CABG typically requires access to the heart, blood vessels and associated tissue. Access to the patient's thoracic cavity may be achieved in an open procedure by making a large longitudinal incision in the chest. This procedure, referred to as a median sternotomy, requires a saw or other cutting instrument to cut the sternum and allow two opposing halves of the rib cages to be spread apart. U.S. Pat. No. 5,025,779 to Bugge discloses a retractor which is designed to grip opposite sternum halves and spread the thoracic cavity apart. The large opening which is created by this technique enables the surgeon to directly visualize the surgical site and perform procedures on the affected organs. However, such procedures that involve large incisions and substantial displacement of the rib cage are often traumatic to the patient with significant attendant risks. The recovery period may be often traumatic to the patient with significant attendant risks. The recovery period may be extensive and is often painful. Furthermore, patients for whom coronary surgery is indicated may need to forego such surgery due to the risks involved with gaining access to the heart.

U.S. Pat. No. 5,503,617 to Jako discloses a retractor configured to be held by the surgeon for use in vascular or cardiac surgery to retract and hold ribs apart to allow access to the heart or a lung through an operating window. The retractor includes a rigid frame and a translation frame slidably connected to the rigid frame. Lower and upper blades are rotatably mounted to the rigid frame and the translation frame respectively. The window approach enables the surgeon to gain access through a smaller incision and with less displacement of the ribs, and consequently, less trauma to the patient.

Once access to the thoracic cavity has been achieved, surgery on the heart may be performed. Such procedures typically require that the heart beat be arrested while maintaining circulation throughout the rest of the body. Cardioplegic fluid, such as potassium chloride (KCl) is delivered to the blood vessels of the heart to paralyze the myocardium. As disclosed in WO 95/15715 to Sterman et al. for example, cardioplegic fluid is infused into the myocardium through the coronary arteries by a catheter inserted into the ascending aorta. Alternatively, cardioplegic fluid is infused through the coronary veins in a retrograde manner by a catheter positioned in the interior jugular vein accessed at the patient's neck. Such procedures require the introduction of multiple catheters into the blood vessels adjacent the heart, which is complicated procedure requiring that the desired vessels be properly located and accessed. The progression of the guide wires and catheters must be closely monitored to determine proper placement. Furthermore, the introduction of catheters forms punctures in the blood vessels that must be subsequently closed, and there is an increased risk of trauma to the interior walls of the vessels in which the catheters must pass.

Alternatively, the CABG procedure may be performed while the heart is permitted to beat. A surgical instrument is used to stabilize the heart and restrict blood flow through the coronary artery during the graft procedure. Special care must be given to procedures performed on a beating heart, e.g. synchronizing procedures to occur at certain stages in the cardiac cycle, such as between heartbeats.

To perform the CABG procedure, the harvested vessel segment, such as the IMA, is grafted to the coronary artery by end-to-side anastomosis. Typically, sutures are used to graft the vessel segments. However, conventional suturing is complicated by the use of minimally invasive procedures, such as the window approach. Limited access and reduced visibility may impede the surgeon's ability to manually apply sutures to a graft. Additionally, it is difficult and time consuming to manually suture if the CABG procedure is being performed while the heart is beating as the suturing must be synchronized with the heart beat.

The process of manually suturing the harvested vessel segment to a coronary artery is time consuming and requires a great deal of skill on the part of the surgeon. The resulting sutured anastomosis will also be dependent on the skills of the surgeon. In minimally invasive procedures, the ability to suture is even more complicated due to limited maneuverability and reduced visibility. Therefore, a need exists for an apparatus and a procedure that enables the remote anastomosis of vessels during both conventional and minimally invasive procedures in a consistent, easier and rapid manner.

SUMMARY

The present disclosure is directed to an instrument for end-to-side anastomosis of first and second blood vessels. The instrument has a handle and a body portion extending distally from the handle. A fastener support or collet is positioned adjacent a distal end portion of the body portion and defines a passage therethrough for the reception of an end of a first blood vessel. A plurality of surgical fasteners are releasably supported by the collet and preferably are radially oriented about the distal end thereof. A fastener closing (camming) member or anvil is mounted proximal of the collet. The camming member and support are relatively slidable in response to actuation of the handle to simultaneously deform the surgical fasteners.

In a preferred embodiment the passage in the support is laterally offset from the body portion. The support defines a longitudinal axis and has a distal end angularly disposed with respect to the longitudinal axis. The support and the fastener forming member may each be composed of at least two separable components. The components may be secured together by a lock which is remotely actuated adjacent the handle.

The surgical instrument may alternately comprise a ring releasably mounted at the support distal end. The ring supports the plurality of surgical fasteners. The surgical fasteners may each have a leg radially oriented about the distal end of the support and proximally extending there from.

A method for end-to-side anastomosis of first and second blood vessels is also disclosed. The method includes providing a surgical instrument having a fastener support or collet defining a passage therethrough for reception of a first vessel. A plurality of surgical fasteners, each having at least one leg, are provided which are releasably supported by the support at a distal end thereof. A fastener forming member or anvil is provided which is mounted adjacent the support, and the fastener forming member and the support are relatively slidable in response to actuation of the handle to simultaneously deform a leg of each of the surgical fasteners.

The method further includes positioning an end of the first vessel through the passage and everting the vessel over a distal end of the support adjacent the plurality of surgical fasteners. The first vessel is then engaged with each of the surgical fasteners. The distal end of the support is inserted to mount the end of the first vessel into an opening in the second vessel. The surgical fasteners engage the side wall of the second vessel adjacent the opening. A leg of the surgical fasteners is simultaneously deformed to secure the first and second vessels together.

The first vessel is then released from the support and in preferred embodiment, the step of releasing the first vessel includes separating the components of the support and of the fastener former. The surgical instrument is sized and configured to be percutaneously inserted to the operative site adjacent the first and second blood vessels.

These and other features of the surgical instrument will become more readily apparent to those skilled in the art from the following detailed description of preferred embodiments of the subject disclosure.

BRIEF DESCRIPTION OF THE DRAWINGS

Various embodiments of the subject surgical apparatus and method are described herein with reference to the drawings wherein:

FIG. 1 is a perspective view of a surgical instrument constructed in accordance with a first embodiment of the subject disclosure;

FIG. 1A is an enlarged perspective view of the surgical instrument of FIG. 1, illustrating the anvil assembly in a closed, unlocked configuration;

FIG. 2 is a perspective view of the surgical instrument, illustrating a lock knob on the handle;

FIG. 2A is an enlarged perspective view of the surgical instrument, illustrating the anvil assembly in a closed, locked configuration;

FIG. 3 is a perspective view with parts separated of the surgical instrument of FIG. 1;

FIG. 3A is an enlarged perspective view with parts separated of the anvil assembly;

FIG. 6 is an enlarged side view in partial cross-section of the anvil assembly, illustrating the anvil in a proximal position;

FIG. 7 is a cross-sectional view of the handle assembly, illustrating the levers in an approximated configuration;

FIG. 8 is an enlarged side view in partial cross-section of the anvil assembly, illustrating the anvil in an intermediate position with respect to the collet;

FIG. 9 is an enlarged side view in partial cross-section of the anvil assembly, illustrating the anvil in a distal position, crimping closed the clips supported by the collet;

FIG. 10 is a top view, illustrated in reduced scale, of a surgical retractor placed on a patient's chest to provide access to the heart;

FIG. 11 is an enlarged top view of the anvil assembly, illustrating the insertion of the harvested vessel into a passage in the anvil assembly;

FIG. 12 is an enlarged top view of the anvil assembly, illustrating the eversion of the harvested vessel about the collet and the clips held thereby;

FIG. 13 is a top view in reduced scale of the surgical instrument with the harvested vessel mounted therein;

FIG. 14 is an enlarged perspective view of the harvested vessel everted on the anvil assembly positioned adjacent a slit in the coronary artery;

FIG. 15 is an enlarged perspective view in partial cross-section illustrating the anvil assembly and everted harvested vessel partially inserted within the coronary artery;

FIG. 16 is a cross-sectional view taken along line 16—16 of FIG. 15, illustrating the position of the clips with respect to the vessels to be joined;

FIG. 17 is a side view in partial cross-section, illustrating the distal advancement of the anvil in order to crimp closed the clips;

FIG. 18 is an enlarged perspective view of the anvil assembly in an open configuration to release the harvested vessel subsequent to the anastomosis; and FIG. 19 is an enlarged top view of the heart, illustrating the completed graft of the harvested vessel to the coronary artery.

FIG. 21 is an enlarged perspective view of an anvil assembly constructed in accordance with a second alternate embodiment of the subject disclosure;

FIG. 22 is a cross-sectional view of the anvil assembly taken along line 22—22 of FIG. 21;

FIG. 23 is a cross-sectional view of the anvil assembly of FIG. 21, illustrating the eversion of a vessel and the mounting of the vessels to be joined on the clips;

FIG. 24 is a cross-sectional view of the anvil assembly, illustrating the crimping of the clips by the moving anvil;

FIG. 25 is an enlarged perspective view of an anvil assembly constructed in accordance with a third alternative embodiment of the subject disclosure;

FIG. 26 is a cross-sectional view taken along line 26—26 of FIG. 25, illustrating the anvil at a proximal position;

FIG. 26A is an enlarged cross-sectional view of the anvil assembly of FIG. 25;

FIG. 27 is a cross-sectional view of the anvil assembly, illustrating the moving anvil crimping the barbed portions of the anastomosis ring;

FIG. 27A is an enlarged cross-sectional view, illustrating the anvil configuration of FIG. 27;

FIG. 28 is a perspective view, illustrating the separation of the anastomosis ring from the anvil assembly;

DETAILED DESCRIPTION OF PREFERRED EMBODIMENTS

Figure 4:
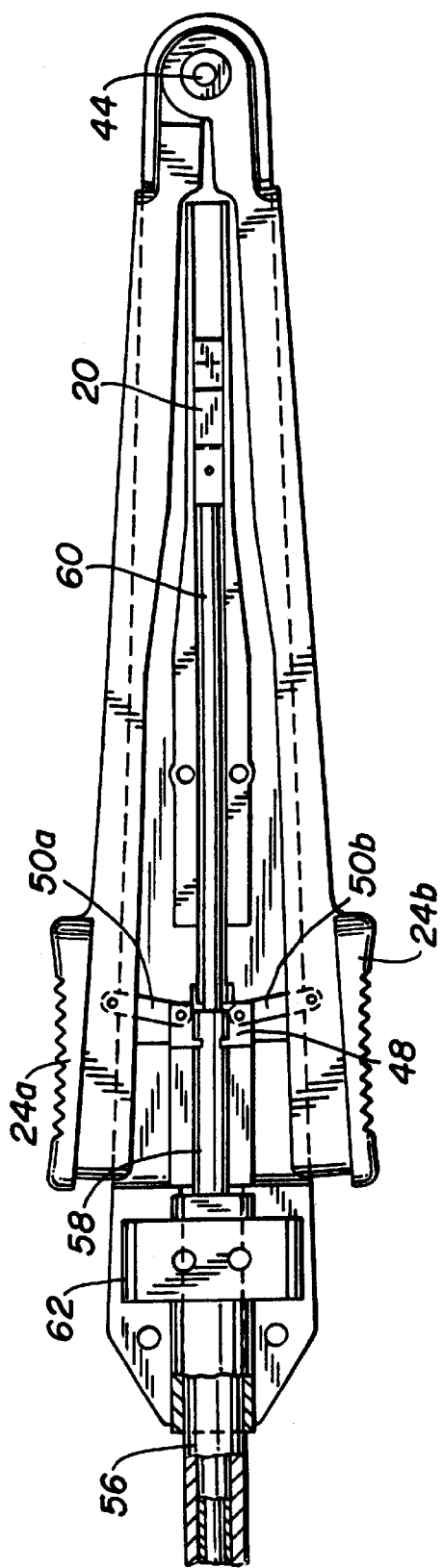
FIG. 4 is a cross-sectional view of the handle assembly taken along line 4—4 of FIG. 1, illustrating the levers in a spaced apart configuration.

The preferred embodiments of the apparatus and method disclosed herein will be discussed in terms of minimally invasive vascular grafts to the coronary artery. However, the subject apparatus may also find use in performing anastomosis of other tubular or luminal body structures.

In the drawings and in the description which follows, the term "proximal," as is traditional, will refer to the end of the apparatus which is closer to the operator, while the term "distal" will refer to the end which is furthest from the operator.

Referring now in detail to the drawings in which like reference numerals identify similar or identical elements, a first embodiment of the subject disclosure is illustrated in FIG. 1, and is designated generally by reference numeral 10. Surgical instrument 10 includes handle assembly 12, body portion 14, and an anvil assembly 16. Surgical instrument 10 is configured to receive a harvested vessel, e.g. the internal mammary artery (IMA), through passage 18 in anvil assembly 16. The IMA is everted and joined to a coronary artery (not shown) by applying a series of clips thereto. The clips, which are supported on anvil assembly 16, are deformed simultaneously by actuation of the handle assembly 12 as will be described in greater detail below. Anvil assembly 16 is configured to release the IMA subsequent to the anastomosis.

Handle assembly 12 includes lock knob 20 positioned on housing or frame 22 configured to remotely secure anvil assembly 16 in a locked configuration surrounding the IMA. Lock knob 20 is illustrated in FIG. 1 in a first, proximal position corresponding to an unlocked configuration of anvil assembly 16. Handle assembly 12 also includes a pair of levers 24a and 24b mounted on frame 22 to advance a fastener closing (camming) member or anvil 26 and thereby close clips supported on collet or support 28 to secure tissue held at anvil assembly 16. It is also contemplated that collet 28 can be movable with respect to anvil 26.

Turning now to FIG. 1A, anvil assembly 16 includes a support, illustratively in the form of collet 28, and a fastener forming member or anvil 26. Since collet 28 is configured to receive the IMA or other harvested vessel through passage 18, collet 28 and anvil 26 are laterally offset from body portion 14. Collet 28 and anvil 26 define a longitudinal axis substantially parallel to the longitudinal axis of body portion 14 (See also, FIG. 11). The distal end portion of collet 28 includes a plurality of longitudinal grooves 30 configured to support a plurality of surgical fasteners or clips 32 held therein by friction. The distal portion of anvil 26 has an annular camming surface 34 disposed along the inner periphery for closing clips 32 upon distal advancement of anvil 26. As will be described below, collet 28 and anvil 26 are each composed of two halves that are pivotably secured by pivot pins 37 and 36, respectively (See, e.g. FIG. 3A). Locking pin 38 (illustrated in phantom) is actuated by lock knob 20. When locking pin 38 is disposed in a proximal position, each of two halves of collet 28 and anvil 26 are freely pivotable about respective pivot pins 37 and 36.

Turning now to FIG. 2, lock knob 20 is moved to a second, distal position with respect to frame 22. As illustrated in FIG. 2A, locking pin 38 is moved distally with lock knob 20 and passes through bore 40 in anvil 26, thereby maintaining both anvil 26 and collet 28 (which is surrounded by anvil 26) in the closed and locked configuration.

FIGS. 3—3A illustrate the components of surgical instrument 10. As illustrated in FIG. 3, frame 22 includes left and right housing portions 42a and 42b respectively, in which the components of handle portion 12 are positioned. Housing portions are secured together by sonic welding or other known means. Levers 24a and 24b are mounted to housing portions 42a and 42b by pin 44 which permits pivotal motion of each of levers 24a and 24b with respect to frame 22.

The distal portion of levers 24a and 24b are secured to linkage 46 which consists of slide 48 and links 50a and 50b. Each of links 50a and 50b has a first end pivotably connected to levers 24a and 24b respectively, by pins 52a and 52b. A second end of each of links 50a and 50b is pivotably mounted to slide 48, such that relative movement of levers 24a and 24b about pin 44 will cause slide 48 to move longitudinally in channel 54 integrally formed in housing portions 42a and 42b. More particularly, approximation of levers 24a and 24b will displace slide 48 distally, while spacing of levers 24a and 24b will displace slide 48 proximally. A spring or other biasing element (not shown) may be interposed between levers 24a and 24b to normally bias levers 24a and 24b apart and thereby bias slide 48 in a proximal position.

Elongated body 14 includes a plurality of generally coaxial elements including outer sleeve 56, drive sleeve 58 and locking bar 60. Outer sleeve 56 is mounted adjacent the distal end portion of frame 22. In particular, the proximal end portion of outer sleeve 56 is secured by pins 64a and 64b positioned within adapter 62, which, in turn, is disposed within recess 66 in housing portions 42a and 42b. The distal end portion of outer sleeve 56 supports anvil assembly 16.

Drive sleeve 58 is coaxially slidable within outer sleeve 56. The proximal end portion of drive sleeve 58 is fixedly secured to slide 48 and is longitudinally slidable therewith in response to actuation of levers 24a and 24b. The distal end portion of drive sleeve 58 is mounted to anvil 26, as will be described in greater detail below.

Locking bar 60 is coaxially slidable within drive sleeve 58. The proximal end portion of locking bar 60 is connected to lock knob 20 by pin 68 extending through openings 61. Lock knob 20 is longitudinally slidable within channel 70 formed in housing portions 42a and 42b. Tab 72 of lock knob 20 protrudes axially through window 74 defined in housing portion 42b to facilitate actuation by the surgeon. The distal end portion of locking bar 60 supports locking pin 38, which preferably has a smaller diameter than locking bar 60 and is axially offset therefrom (See Also, FIGS. 1A, 2A). Longitudinal movement of lock knob 20 facilitates the locking and unlocking of anvil assembly 16 as will be described below.

Turning now to FIG. 3A, the components of anvil assembly 16 are separable for release of a harvested vessel subsequent to anastomosis. Collet 28 consists of an upper collet portion 78a and a lower collet portion 78b. Upper collet portion 78a includes collar 80 for mounting to outer sleeve 56 (not shown). Collar 80 further defines bore 82 through which various components are inserted. Upper collet portion 78a and lower collet portion 78b each define a bore 84 and 86 respectively, through which pivot pin 37 is inserted to facilitate relative pivoting of collet portions 78a and 78b. As discussed above, collet portions 78a and 78b together define a passage 18 through which the harvested vessel may pass. Each of clips 32 has a first leg 94 configured to be received in and secured in longitudinal groove 30 and a second leg or prong 96 having sharpened tip 98. Prongs 96 are disposed along the outer periphery of collet 28 adjacent the distal edge or lip 29. Lip 29 is disposed at an angle a with respect to the longitudinal axis of collet 28 in order to provide the proper angle for the anastomosis of the IMA into the LAD (See, FIG. 6). Angle a is preferably between 30° and 60° in order to improve blood flow from the IMA into the LAD, and may reduce the risk of embolism. Other angles are also contemplated. Prongs 96 are generally aligned with the longitudinal axis of collet 28 and extend both radially outwardly from collet 28 and proximally from lip 29.

Anvil 26 includes upper anvil portion 100a and lower anvil portion 100b mounted proximal of collet 28. The distal end portion of drive sleeve 58 passes through bore 82 in collet 28 and is connected to clevis portion 102 of upper anvil portion 100a, and is longitudinally movable therewith in response to actuation of levers 24a and 24b. Spaced apart shackles 104a and 104b receive shackle 106 of lower anvil portion 100b. Flange 104C fits into drive sleeve 58. Pivot pin 37 passes through bores 110a and 110b of shackles 104a and 104b respectively, and bore 112 of shackle 106 to permit pivotal movement of lower anvil portion 100b with respect to upper anvil portion 100a. As described above, camming surface 34 is defined along the inner, distal periphery of each of collet portions 100a and 100b to crimp clips 32 by contacting prongs 96 as will be described below.

Upper anvil portion 100a and lower anvil portion 100b of movable anvil 26 are remotely locked in the closed position by locking pin 38 passing through bores 40a and 40b in upper anvil portion 100a and bore 118 in lower anvil portion 100b. Locking pin 38 has a rounded end 120 to facilitate passage of locking pin 38 through bores 40a, 40b, and 118.

Movable levers 24a and 24b are disposed in a spaced apart configuration. Slide 48 is positioned in a proximal position (FIG. 4) within channel 54, in a slightly "over-center" configuration with respect to links 50a, 50b. Drive sleeve 58 is disposed proximally with respect to outer sleeve 56. Passage 18 is laterally offset from body portion 14 (illustrated in phantom in FIG. 5). When locking pin 38 is disposed in bores 40a, 40b and 118, anvil 26 surrounds collet 28 and maintains it in a closed configuration as well.

Figure 5:
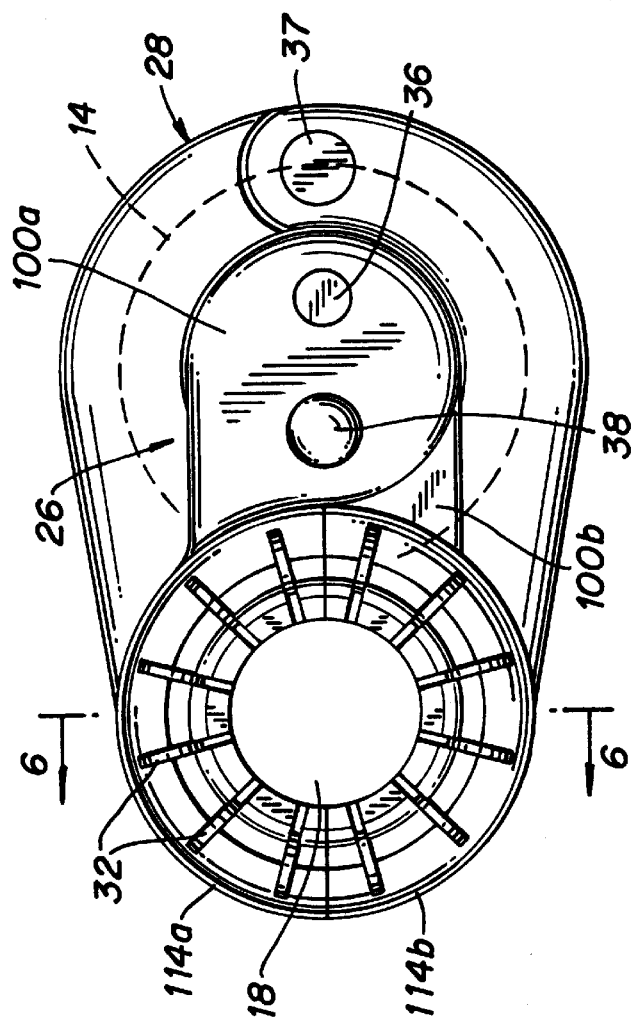
FIG. 5 is an enlarged end view of the anvil assembly.

The orientation of anvil 26 with respect to collet 28 shown in FIG. 6 corresponds to the spaced apart configuration of levers 24a and 24b of FIG. 4. Anvil 26 is positioned in a proximal position with respect to collet 28. A peripheral recess 122 is formed in the outer surface of collet portions 78a and 78b for reception of tissue, as will be described below. Peripheral ridge 124 is disposed along the interior portion of anvil 26. Ridge 124 applies a compressive force on collet 28 to tightly retain clips 32.

Approximation of levers 24a and 24b remotely actuates movable anvil 26. Given the initially "over-center" position of slide 48, moving levers 24a and 24b together moves slide 48 distally through motion of links 50a and 50b. Slide 48 moves drive sleeve 58 distally as indicated by the arrow in FIG. 7.

Distal advancement of drive sleeve 56 (not shown) advances anvil 26 towards clips 32. With reference to FIG. 8, curved camming surface 34 initially contacts point 98 of prong 96. As shown in FIG. 9, further distal movement of camming surface simultaneously crimps prongs 96 down towards legs 94, thereby closing clips 32. After prongs 96 have been crimped, ridge 124 moves into recess 122, thereby relieving the compressive force on collet 28 and clips 32 held therein. Alternatively, collet 28 is slidably mounted and moved proximally with respect to anvil 26 in order to crimp clips 32.

Operation of the Instrument

Turning now to FIGS. 10–20, the operation of surgical instrument 10 will now be described. Surgical instrument 10 may be used in conventional open CABG procedures using a median sternotomy or other large incision without stopping the heart. Alternatively, the thoracic "window" procedure may be used to achieve access. The "window" approach involves a smaller incision and less displacement of the ribs, and therefore is less traumatic to the patient. For this approach, conventional surgical techniques are used to determine the location of the incision I accessing chest cavity C. A surgical retractor, such as surgical retractor SR is used to access the heart and coronary arteries by creating the "window". Base B is placed on the chest of the patient with the opening of base B overlying the operative site. Incision I is made, exposing several ribs $R_3$, $R_4$, $R_5$, $R_6$.

Retractor assemblies RA are mounted to base B at various locations. Each of retractor assemblies RA includes blade BL having a hook to engage a rib therewith. Blade BL is positioned around a rib, which is deflected and retracted by moving blade BL radially outward. Additional retractor assemblies RA are mounted and used to retract ribs until a sufficiently large opening O in chest cavity C is defined to provide access to the heart. For example, sternum S and fourth rib $R_4$ and fifth rib $R_5$ can be spread apart to create a window. Alternatively, fourth rib $R_4$ and fifth rib $R_5$ are cut from sternum S and spaced to create a larger window as shown in FIG. 10. Alternatively, a fifth rib $R_5$ can be cut, and sternum S and fourth rib $R_4$ and sixth rib $R_6$ are spread. Base B is at least partially held in position over the operative site by tension created in retracting the ribs by retractor blades BL.

The internal mammary artery IMA is dissected from surrounding cartilage and muscle, and a free end is exposed. The coronary artery, e.g. the left anterior descending artery LAD, is then prepared for receiving IMA graft. The heart H is positioned either by traction sutures passing through the pericardium or by manipulation instruments which are held by surgical personnel or clamped to the operating table or to base B. Blood flow through the LAD can be restricted by cardiopulmonary bypass and pericardial cooling. Alternatively, a clamping instrument may be applied directly on the LAD to restrict blood flow and reduce movement of the heart near the LAD.

The IMA is prepared for grafting to the LAD. Anvil 26 and collet 28 are locked by advancement of locking pin 38. A free end of the IMA is inserted through passage 18 in collet 28, such that the end of the IMA protrudes beyond the distal end portion of collet 28 as shown in FIG. 11. Alternatively, the IMA may be inserted into collet 28 prior to locking anvil assembly 16.

Next, as shown in FIG. 12, the free end of the IMA is everted around the lip portion 29 of collet 28. In particular, tweezers T may be used to manually evert the IMA. Alternatively, a remotely actuated grasping instrument such as ENDO-GRASP instrument manufactured by United States Surgical Corporation of Norwalk, Conn., may be used. The IMA is grasped and stretched over collet portions 78a and 78b (not shown). Points 98 of prongs 96 are configured to pierce the IMA and hold the vessel in place. Care should be exercised to insure that the IMA has been engaged by each of prongs 96. The elasticity of the IMA provides a compression about collet 28 in the everted configuration.

FIG. 13 illustrates the LAD prepared to receive the IMA. An incision I$_L$ is made in the LAD downstream from the occlusion. Surgical instrument 10 is manipulated such that anvil assembly 16 carrying the everted IMA is approximated with incision I$_L$ in the LAD.

The everted IMA is inserted into incision I$_L$ of the LAD (FIG. 14). The distal edge 29 of collet 28 is configured with an angle in order to optimize the end-to-side anastomosis and to facilitate blood flow across the graft from the IMA to the LAD. This junction creates "heel" H and "toe" T (FIG. 16) portions in which an acute or obtuse angle between the vessels is defined.

Turning to FIG. 15, the distal end portion of collet 28 including everted IMA and clips 32 are inserted into incision IL in the LAD. The proximally extending angular orientation of prongs 96 permits clips 32 to be inserted atraumatically into the LAD. Elasticity of the LAD closes incision I$_L$ about collet 28.

Upon insertion, the surgeon retracts anvil assembly 16 to apply proximal force to surgical instrument 10. Such force permits sharpened points 96 to pierce the side wall of the LAD surrounding incision I$_L$ (FIG. 16). By retracting anvil assembly 16, incision I$_L$ is forced to assume a circular shape corresponding to collet 28 and makes uniform contact with the everted section of IMA. The LAD is also partially everted as shown. The symmetrical nature of the circular junction of IMA and LAD permits the consistent joining of the vessels about collet 28, including "heel" H and "toe" T. Distal advancement of camming surface 34 of anvil 26 forms clips 32 about the IMA and LAD (FIG. 17). As can be appreciated, the IMA and LAD are clipped in intima to intima contact. This reduces the chances of thrombosis and restenosis.

After the surgeon ascertains that a complete graft has been performed and that all of clips 32 have been properly formed, the surgeon may then release anvil assembly 16 from the IMA as described above by withdrawing locking pin 38 proximally from bores 116a, 116b, and 118 of anvil 26. Lower anvil portion 100b of anvil 26 is permitted to pivot open with respect to upper anvil portion 100a. This permits lower collet portion 78b to open, thereby freeing the IMA from anvil assembly 16 as shown in FIG. 18.

As illustrated in FIG. 19, the completed graft permits increased blood flow downstream from the occlusion. Any clamps on the IMA may be removed. If cardiopulmonary bypass is used, it is gradually removed. Alternatively, a clamp used on the coronary artery to restrict blood flow is removed and normal blood flow is permitted to resume.

Figure 20:
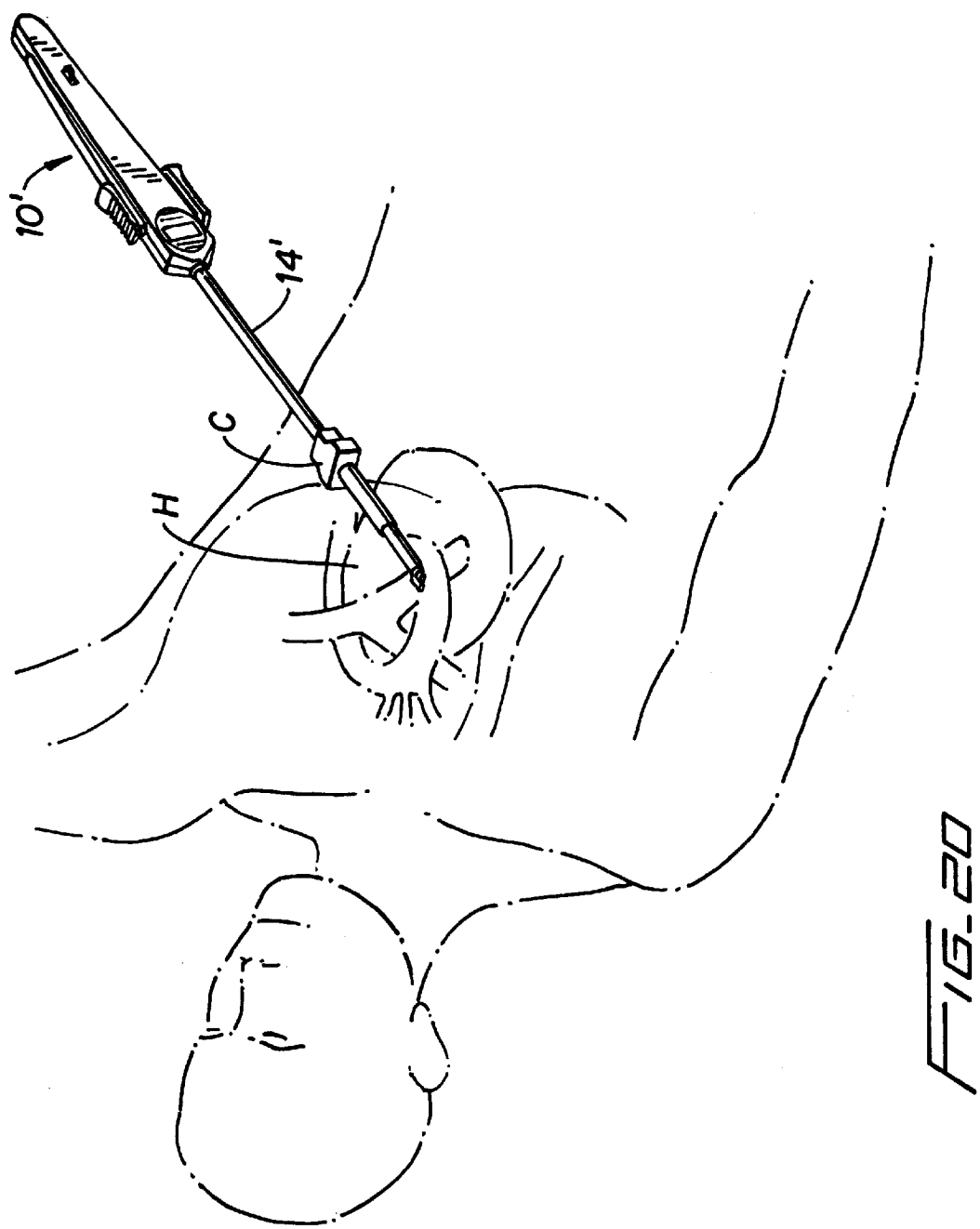
FIG. 20 is a side view showing insertion of an endoscopic version of the surgical instrument of FIG. 1 through a cannula.

Surgical instrument 10 may also have particular use for example in minimally invasive CABG procedures such as thoracoscopic procedures for grafting the IMA to the LAD, etc. As shown in FIG. 20, instrument 10' is provided with body portion 14' configured and dimensioned to be inserted through cannula C placed between the ribs. A thoracoscope (not shown) is likewise inserted through a second cannula in order to illuminate and visualize the procedure.

It should be noted that use of the aforedescribed instruments in other procedures is also contemplated.

A Second Alternate Embodiment of the Subject Instrument

Turning now to FIGS. 21–24, a second alternate embodiment of the surgical instrument is disclosed at reference numeral 200. Instrument 200 operates substantially as described above with regard to instrument 10, with the differences described hereinbelow. Instrument 200 may be used in conventional open procedures, as well as with the minimally invasive "window" approach (FIGS. 10–19) and the thoracoscopic approach of FIG. 20. Surgical instrument 200 has body portion 14 and anvil assembly 216. Passage 218 extends longitudinally through anvil assembly 216. A plurality of "C"-shaped surgical fasteners or clips 232 are supported on collet 228 to pierce vessel segments to be joined. Anvil 226 is advanced against clips 232 to secure such clips on the tissue to be joined. Collet 226 and anvil 228 are each configured to release the vessel subsequent to the anastomosis. Collet 226 and anvil 228 are each constructed of separable halves as described above in FIG. 3A for release of the IMA subsequent to the graft.

As described above with respect to anvil assembly 16, collet 228 is supported at the distal end portion of outer sleeve 56. Anvil 226 is mounted to the distal end portion of driver sleeve 58 which is actuable by moving levers 24a and 24b (not shown).

Distal portion of collet 228 includes a distal lip 230 which has angle with respect to the longitudinal axis to facilitate the proper relative orientation between the vessels joined. This angle is preferably between 30 and 60 degrees. The plurality of clips 232 are supported within longitudinal channels 236 formed along collet 228. Each of clips 232 has a generally "C"-shape, including a crown portion 238 that rests within channel 236, a sharpened leg or prong 240 and a blunt or curved-end leg 242. Clips 232 are disposed around collet 228 such that prongs 240 extend proximally and radially outwardly in order to pierce the vessels to be joined as described above with respect to surgical instrument 10.

Anvil 226 surrounds tubular portion of collet 228 and includes a plurality of longitudinally aligned camming members 246 which are at least partially slidable within channel 236. Each camming member 246 includes a camming surface 248 on a distal end portion thereof for simultaneously closing clips 232 about vascular tissue, as will be described below.

Anvil assembly 216 can be used to join the LAD and IMA in intima to intima contact substantially as described above with respect to FIGS. 10–16, with the differences noted below. The free end of the IMA (shown in phantom in FIG. 23) or other harvested vessel is inserted through passage 218 of collet 228. A distal end portion of the IMA is everted over lip 230 and pierced by prongs 240 of each of clips 232. Tweezers or a remotely actuable grasping instrument is used to evert the IMA. Care should be taken to insure that prong 240 of each clip 232 is firmly inserted in IMA. The distal end portion of anvil assembly 216 is inserted into an incision in the LAD or other coronary artery and retracted slightly such that each of sharpened legs 240 pierce the LAD (illustrated in phantom). Visual inspection should be to verify that such piercing has occurred.

As illustrated in FIG. 24, actuation of levers 24a and 24b (not shown) operably advances anvil 226 including camming member 246 distally. Camming surfaces 248 engage proximal legs 242 and compress clip 232, thereby approximating legs 240 and 242 and trapping vascular tissue therebetween. Clips 232 and camming surfaces 248 may be configured such that legs 240 and 242 cross in order to further secure clips 232 to the vessel. After the surgeon has verified that an acceptable graft has been made, collet 228 and anvil 226 are unlocked by lock knob 20 and opened to release IMA as described above in FIG. 18.

A Third Alternate Embodiment of the Subject Instrument

Turning now to FIGS. 25–29, a third alternate embodiment of the surgical instrument is disclosed at reference numeral 300. Instrument 300 operates substantially as described above with regard to instrument 10 above, with the differences described hereinbelow. Instrument 300 may be used in conventional open procedures as well as with the minimally invasive "window" approach (see, FIGS. 10–19) and with the thoracoscopic procedure of FIG. 20. Surgical instrument 300 has body portion 14 and anvil assembly 316. Passage 318 extends longitudinally through anvil assembly 316. Collet 328 supports ring member 332 having a plurality of surgical fasteners or barbs 334 for piercing and securing vessels to be joined. Both anvil 326 and collet are each composed of two components and hinged at pivot pins 336 and 338 respectively, to facilitate insertion of the IMA into passage 318 and removal of anvil assembly 316 from the IMA subsequent to the anastomosis.

Collet 328 is supported at the distal end portion of outer sleeve. Movable anvil 326 is mounted at a distal end portion of driver sleeve 58 and longitudinally movable therewith and actuated by levers 24a and 24b (not shown).

The distal end portion of collet 228 includes angled lip 350 defining an angle a with the longitudinal axis for properly positioning the IMA with respect to the LAD. Ring 332 is supported on collet 228 adjacent lip 350. Ring 332 may be provided with channel 352 for receiving peripheral bead 354 (See Also, FIG. 27A). The distal end portion of tubular portion 278 includes a plurality of flanges 353 separated by longitudinal grooves 354 which permit a degree of compression and expansion of the diameter of lip 350. Anvil 226 includes stepped bore 340 surrounding collet 228. Stepped bore 340 includes camming ridge 356 configured to engage peripheral camming surface 358 and thereby compress collet 228 and effectively reduces diameter of lip 350. Ring 332 may thereby be released from bead 354 as will be described below.

The IMA (illustrated in phantom in FIG. 26) is inserted through passage 318 and everted over lip 350 and pierced by barbs 334. The distal end portion of tubular portion 378 including ring 332 and the everted portion of the IMA are inserted into an incision in the LAD (illustrated in phantom) as described above with respect to FIGS. 10–16. Anvil assembly 316 is retracted slightly such that each of barbs 334 pierce the LAD.

Anvil 326 is advanced in response to actuation of levers 24a and 24b (FIG. 27). The distal portion of anvil 326 includes a curved camming surface 380 which deforms prongs 334 radially inward towards ring 332, thereby securing the IMA and LAD together in intima to intima contact. Alternatively, collet 328 is slidable with respect to anvil 326.

Camming ridge 356 and camming surface 358 are configured to relatively engage following crimping of barbs 334. Camming surface 358 expands outward distally such that distal advancement of camming ridge 356 against camming surface 358. Flanges 353 are forced into approximation, thereby reducing the effective diameter of lip 350 and displacing bead 354 radially inward to permit ejection of ring 332 from anvil assembly 316.

Instrument 300 is withdrawn from the anastomosis junction as shown in FIG. 28. Anvil assembly 316 is remotely unlocked as described above with respect to FIG. 18 and opened to release IMA positioned within passage 318.

Figure 29:
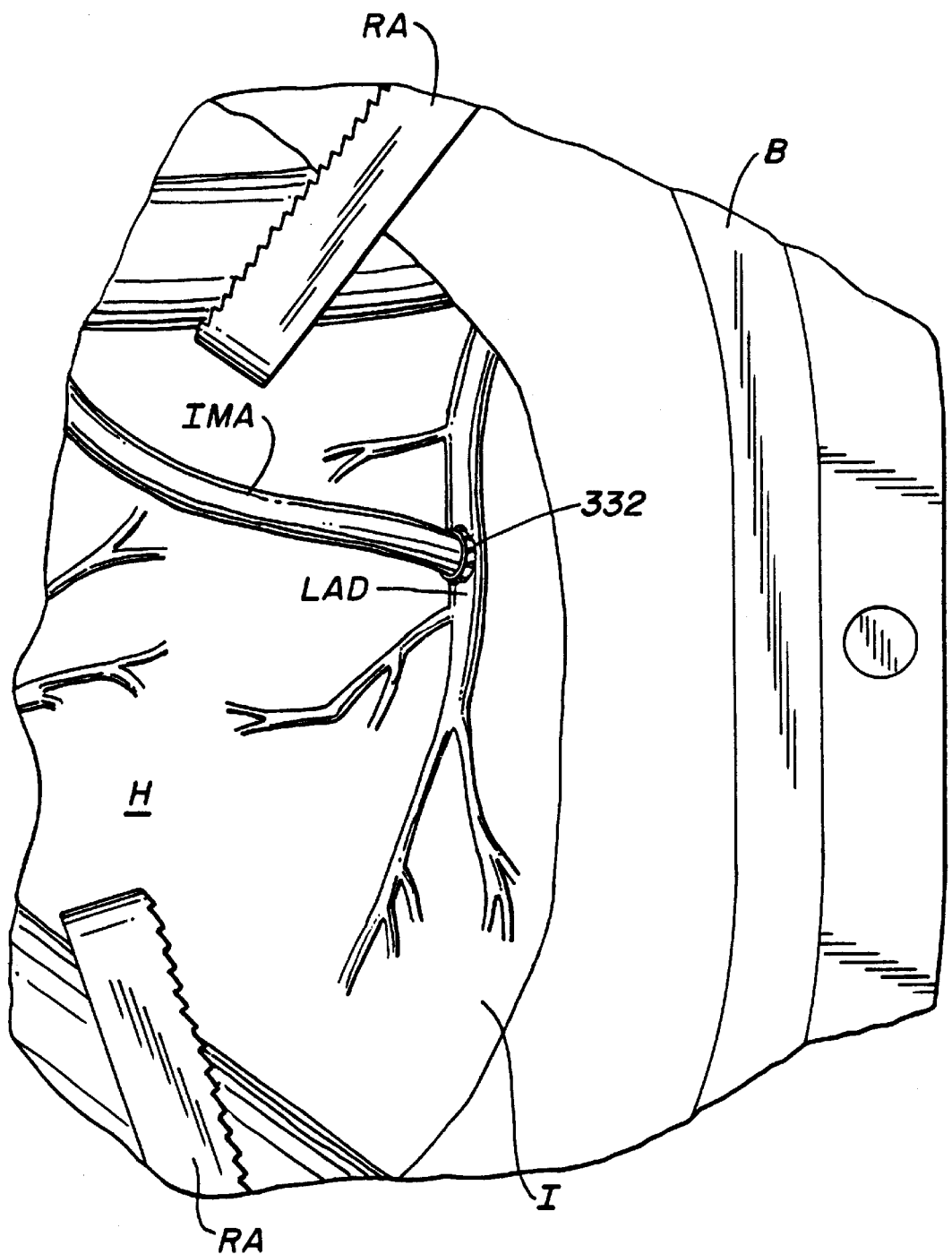
FIG. 29 is an enlarged view of the patient's heart, illustrating the anastomosis ring at the graft junction.

Anastomosis ring 332 remains in place at the junction of the LAD and the IMA as shown in FIG. 29. Anastomosis ring 332 is preferably constructed from a biocompatible material such as titanium.

Figure 30A:
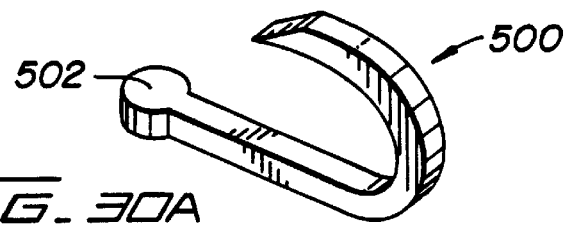
FIGS. 30A–30D illustrate alternate embodiments of the surgical fastener.
Figure 30B:
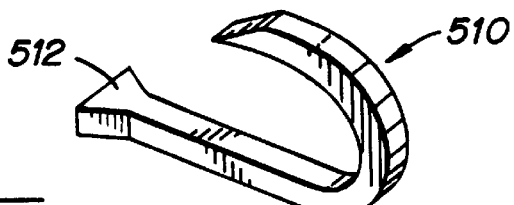
Figure 30C:
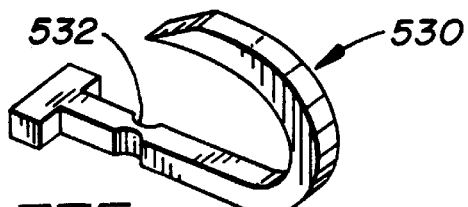
Figure 30C:
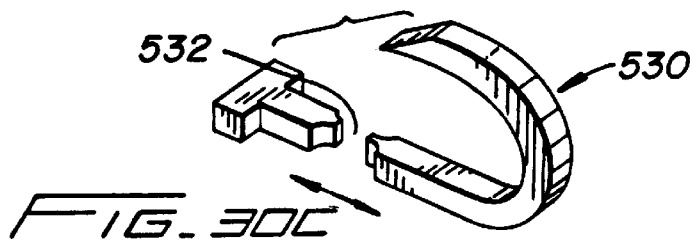
Figure 30D:
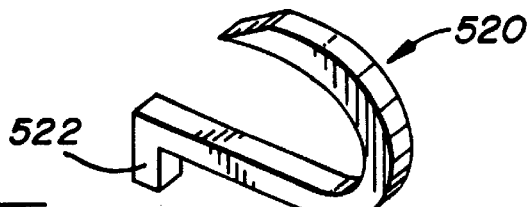

FIGS. 30A–30D illustrate alternative embodiments of the surgical fasteners which include means to enhance their mount to the collet and thus do not rely solely on the frictional fit as described above. The fastener 500 of FIG. 30A includes a "lollypop head" 502, fastener 510 of FIG. 30B has a tapered tip 512 and fastener 520 of FIG. 30D has a L-shaped locking tip 522. These configurations enhance the frictional engagement of the fasteners on the collet. In the embodiment of FIG.30C, fastener 530 has a break-away portion 532 which becomes detached from the fastener as it is deformed by the anvil.

It will be understood that various modifications may be made to the embodiments shown here. For example, the instruments may be sized to perform anastomosis for other vessels and luminal tissue. Therefore, the above description should not be construed as limiting, but merely as exemplifications of preferred embodiments. Those skilled in the art will envision other modifications within the scope and spirit of the claims appended hereto.

What is claimed is:

1. A surgical instrument for anastomosis of first and second blood vessels, which comprises:
   a) a handle;
   b) a body portion extending distally from the handle;
   c) a fastener support positioned adjacent a distal end portion of the body portion, the support defining a passage therethrough for the reception of an end of a first blood vessel and configured to releasably support a plurality of surgical fasteners; and
   d) a camming member mounted proximal of the support, the camming member and support being relatively slidable in response to actuation of the handle to simultaneously deform the surgical fasteners.

2. A surgical instrument as recited in claim 1, wherein the passage in the support is laterally offset from the body portion.

3. A surgical instrument as recited in claim 2, wherein the support defines a longitudinal axis and has a distal edge angularly disposed with respect to the longitudinal axis.

4. A surgical instrument as recited in claim 3, wherein the support and the camming member are each composed of at least two separable components.

5. A surgical instrument as recited in claim 1, which further comprises:
   a ring releasably mounted at the support distal end, the ring supporting the plurality of surgical fasteners.

6. A surgical instrument as recited in claim 5, wherein the surgical fasteners each have a leg radially oriented about the distal end of the support and extending proximally from the ring.

7. A surgical instrument as recited in claim 1, wherein the camming member has a camming surface slidable to engage a leg of the fastener.

8. A surgical instrument for anastomosis of first and second blood vessels, which comprises:
   a) a handle;
   b) a body portion extending from the handle and defining a first central longitudinal axis; and
   c) a fastener support positioned adjacent a distal end portion of the body portion and configured to support a plurality of fasteners, the fastener support defining a second central longitudinal axis being laterally offset from the longitudinal axis of the body portion, and wherein the handle is actuable to form the fasteners.

9. A surgical instrument as recited in claim 8, wherein the fastener support defines a passage therethrough for reception of an end of a first blood vessel.

10. A surgical instrument as recited in claim 8, wherein the support includes a distal edge angularly disposed with respect to the second central longitudinal axis.

11. A surgical instrument as recited in claim 10, further comprising a camming surface for forming a plurality of fasteners and wherein the support and the fastener forming surface are each composed of at least two separable components.

12. A surgical instrument as recited in claim 9, which further comprises:

a ring releasably mounted at the support distal end, the ring supporting the plurality of surgical fasteners.

13. A surgical instrument as recited in claim 12, wherein the surgical fasteners each have a leg radially oriented about the distal end of the support and extending proximally from the ring.

14. A surgical instrument as recited in claim 8, wherein the support is generally cylindrical.

15. A surgical instrument as recited in claim 8, further comprising a plurality of individual surgical fasteners mounted in the support.

16. A surgical instrument for anastomosis of first and second blood vessels, which comprises:

a) a handle;
b) a body portion extending distally from the handle and defining a longitudinal axis;
c) a support positioned adjacent a distal end portion of the body portion, the support configured to releasably support a plurality of surgical fasteners such that the fastener legs extend radially with respect to a longitudinal axis of the support, the support being composed of at least two separable components; and
d) a fastener forming member mounted adjacent the support, the fastener forming member and support being relatively slidable in response to actuation of the handle to simultaneously deform the surgical fasteners.

17. A surgical instrument as recited in claim 16, wherein the support defines a passage therethrough for the reception of an end of a first blood vessel.

18. A surgical instrument as recited in claim 17, wherein the fastener forming member is composed of at least two separable components.

19. A surgical instrument as recited in claim 18, which further comprises:

a lock remotely actuated adjacent the handle to secure together the components of the fastener forming member.

20. A surgical instrument as recited in claim 19, wherein the support defines a longitudinal axis and has a distal edge angularly disposed with respect to the longitudinal axis.

21. A surgical instrument as recited in claim 20, which further comprises:

a ring releasably mounted at the support distal end, the ring supporting the plurality of surgical fasteners.

22. A surgical instrument as recited in claim 21, wherein the support is generally cylindrical.

23. A surgical instrument for anastomosis of first and second blood vessels, which comprises:

a) a handle;
b) a body portion extending distally from the handle;
c) a support positioned adjacent a distal end portion of the body portion, the support defining a longitudinal axis and a passage therethrough for the reception of an end of a first blood vessel, the support configured to releasably support a plurality of surgical fasteners, the support distal end being angularly disposed with respect to the longitudinal axis.

24. A surgical instrument as recited in claim 23, further comprising an fastener forming member mounted adjacent the support, the fastener forming member and support being relatively slidable in response to actuation of the handle to simultaneously deform the surgical fasteners.

25. A surgical instrument as recited in claim 24, wherein the fastener forming member has a camming surface slidable into contact with the fasteners to form the fasteners.

26. A surgical instrument for anastomosis of first and second blood vessels, which comprises:

a) a handle;
b) a body portion extending distally from the handle;
c) a support mounted adjacent a distal end portion of the body portion, the support defining a passage therethrough for the reception of an end of a first blood vessel;
d) a plurality of surgical fasteners having a leg and releasably supported by the support, each surgical fastener having a first position wherein at least a portion of the leg extends proximally from the support; and
e) a fastener forming member mounted adjacent the support, the fastener forming member and support being relatively slidable in response to actuation by the handle to simultaneously deform the surgical fasteners to a second position.

27. A method for anastomosis of first and second blood vessels, which comprises:

a) providing a surgical instrument having a support defining a passage therethrough for reception of a first vessel, a plurality of surgical fasteners releasably supported by the support at a distal end thereof, the surgical fasteners each having a leg, and a fastener forming surface, the fastener forming surface and support being relatively slidable to simultaneously deform the surgical fasteners;
b) positioning an end of the first vessel through the passage and everting the first vessel over the distal end of the support adjacent the plurality of surgical fasteners;
c) engaging the first vessel with the surgical fasteners;
d) inserting the distal end of the support, mounting the end of the first vessel into an opening in a side wall of a second vessel;
e) engaging a side wall of the second vessel adjacent the opening with the surgical fasteners; and
f) simultaneously deforming one leg of each of the surgical fasteners to secure the first and second vessels together.

28. A method as recited in claim 27, wherein the step of engaging the first blood vessel with the surgical fasteners includes piercing the first vessel with the surgical fasteners.

29. A method as recited in claim 28, wherein the step of engaging the second blood vessel with the surgical fasteners includes piercing the second vessel with the surgical fasteners.

30. A method as recited in claim 29, wherein the leg of each surgical fastener has a first position extending proximally from the support, and wherein the step of engaging the first blood vessel with the surgical fasteners includes piercing the first vessel with the legs disposed in the first position.

31. A method as recited in claim 30, which further comprises:

releasing the first vessel from the support.

32. A method as recited in claim 31, wherein the support and the anvil are each composed of at least two separable components, and wherein the step of releasing the first vessel includes at least partially separating the components of the support and the anvil.

33. A method as recited in claim 32, which further comprises:

percutaneously inserting the surgical instrument to the operative site adjacent the first and second blood vessels.

34. A method for anastomosis of first and second blood vessels, which comprises:

a) providing a surgical instrument having a plurality of surgical clips releasably supported by a support at a distal end thereof.

b) everting the first vessel over the distal end of the support adjacent the plurality of surgical fasteners;

c) inserting the distal end of the support and the everted end of the first vessel into an opening in a side wall of a second vessel;

d) manipulating the instrument such that at least a portion of the first and second vessels are in intima to intima contact; and e) advancing a camming member to contact at least one leg of each clip to crimp the surgical clips to secure the first and second vessels together.

35. A method as recited in claim 34 further comprising the step of inserting the first vessel through a passage in the instrument prior to everting the first vessel.

36. A method as recited in claim 35, wherein the step of manipulating the instrument includes piercing the second vessel with the surgical clips.

37. A method as recited in claim 36, wherein the step of deforming the fastener includes sliding a fastener forming surface of the instrument into contact with the fasteners.

38. A method as recited in claim 34, wherein the step of manipulating the instrument includes the step of at least partially everting the second vessel.

* * * * *